(12) United States Patent
Boyer

(10) Patent No.: US 6,322,595 B1
(45) Date of Patent: Nov. 27, 2001

(54) DETERGENT COMPOSITION COMPRISING TWO CELLULASE COMPONENTS, WITH AND WITHOUT A CELLULOSE-BINDING DOMAIN

(75) Inventor: Stanton Lane Boyer, Fairfield, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/230,665

(22) PCT Filed: Jul. 25, 1997

(86) PCT No.: PCT/US97/13194

§ 371 Date: Jan. 29, 1999

§ 102(e) Date: Jan. 29, 1999

(87) PCT Pub. No.: WO98/04663

PCT Pub. Date: Feb. 5, 1998

Related U.S. Application Data

(60) Provisional application No. 60/023,125, filed on Jul. 30, 1996.

(51) Int. Cl.[7] .............................. C11D 3/386; C12N 9/42; D06L 1/00
(52) U.S. Cl. .............................. 8/137; 510/300; 510/320; 510/392; 510/530; 424/94.1; 424/94.61
(58) Field of Search .................................... 510/300, 320, 510/392, 530; 424/94.1, 94.61; 8/137

(56) References Cited

U.S. PATENT DOCUMENTS

| | | | |
|---|---|---|---|
| 4,822,516 | 4/1989 | Suzuki et al. | 252/174.12 |
| 6,268,196 * | 7/2001 | Fowler et al. | 435/209 |

FOREIGN PATENT DOCUMENTS

| | | | |
|---|---|---|---|
| 508358 A1 * | 10/1992 | (EP) . | |
| WO 95/02675 * | 1/1995 | (EP) . | |
| 0 495 257 A1 | 11/1991 | (EP) | C11D/3/386 |
| 0 508 358 A1 | 10/1992 | (EP) | C11D/3/386 |
| 2 075 028 A | 11/1981 | (GB) | C12N/9/42 |
| WO 91/05841 | 5/1991 | (WO) | C11D/3/386 |
| WO 95/02675 | 1/1995 | (WO) | C11D/3/386 |
| WO 91/10732 | 7/1991 | (WO) | C12N/9/42 |
| WO 92/06210 | 4/1992 | (WO) | C12P/21/00 |
| WO 96/23928 | 8/1996 | (WO) | D06M/16/00 |

* cited by examiner

Primary Examiner—Mark Kopec
Assistant Examiner—Brian P. Mruk
(74) Attorney, Agent, or Firm—C. Brant Cook; Kim W. Zerby; Steven W. Miller

(57) ABSTRACT

A detergent composition comprising a combination of cellulase enzymes is provided. The detergent composition comprises at least 1% by weight of a surfactant, at least 1% by weight of a builder and an effective amount of an enzymatic mixture capable of degrading cellulose. The enzymatic mixture comprises a combination of at least two cellulases, of which one is a surface-active cellulase having a cellulose-binding domain, and one is a nonsurface-active cellulase which does not possess a cellulose-binding domain. The nonsurface-active cellulase and the surface-active cellulase are in a weight ratio of from 1:2 to 20:1 in the detergent composition.

26 Claims, No Drawings

DETERGENT COMPOSITION COMPRISING TWO CELLULASE COMPONENTS, WITH AND WITHOUT A CELLULOSE-BINDING DOMAIN

RELATED APPLICATIONS

This application is a 371 of International Application Serial No. PCT/US97/13194 filed Jul. 25, 1997 which claims priority under 35 U.S.C. §119(e) to U.S. Provisional Application Ser. No. 60/023,125 filed Jul. 30, 1996.

FIELD OF THE INVENTION

The present invention relates to detergent compositions comprising a surfactant, builder and an enzymatic mixture. The invention is directed to a detergent composition containing an effective amount of an enzymatic mixture capable of degrading cellulose and made up of a surface-active and a nonsurface-active cellulase (i.e., enzymes that hydrolyze $\beta$-1,4-glucan linkages). The nonsurface-active and the surface-active cellulases are in a weight ratio of from about 1:2 to about 20:1 in the detergent composition. In addition, at least about 1% by weight of the detergent composition is a surfactant and at least about 1% by weight of the detergent composition is a builder.

BACKGROUND OF THE INVENTION

Conventional laundry detergent formulations usually contain surfactants, builders and other additives to improve the removal of soil. It is recognized by those skilled in the art of formulating detergents that enzymes, a unique class of proteins, can be added to conventional laundry detergents to improve the cleaning of textiles. Enzymes are substances formed by living cells which catalyze biochemical reactions, and when used in detergent formulations, they enhance the cleaning ability of laundry detergents. Likewise, it is also known to those skilled in the art that when conventional enzyme-containing laundry detergents are used in the wash process, the surfactant and builder present in the formulation enhance the action of the enzyme. Common enzymes included in conventional laundry detergents include: amylase, which breaks down starch; protease, which catalyzes reactions that break down proteins; lipases which work on lipids; and cellulase which breaks down cellulose.

Cellulases are known in the art as enzymes that hydrolyze cellulose ($\beta$-1,4-glucan linkages) to form glucose, cellobiose, cellooligosaccharides, etc. Celluloytic enzymes are recognized by those skilled in the art of detergent formulation not only as agents that enhance the cleaning ability of detergents but also as agents that soften and improve the feel of cotton. Repeated washing of cotton-containing fabric can result in the fabric assuming a harsh and unpleasant stiffness. The use of laundry detergent formulations containing cellulase can reduce or eliminate the stiffness and harshness of fabrics which contain cotton. In addition cellulase enzymes also assist in maintaining the whiteness of fabrics and can play a role in maintaining colors. Moreover, cellulase enzymes in laundry detergent compositions are employed as stain removers and contribute to the overall impression of cleaning performance perceived by the consumer.

However, it is recognized by those skilled in the art of detergent enzymology that cellulase preparations are complex mixtures of which only a certain fraction is effective as a catalyst in the washing process. For example, the complete fungal cellulase enzyme is composed of multiple components which include exo-cellobiohydrolases, endoglucanases and $\beta$-glucosidases. It can be difficult to optimize the production of multiple enzyme systems since the cost of producing an enzyme which is comprised of a complex mixture can be prohibitive. Fortunately, it is now known that cellulase preparations useful to enhance the cleaning ability of detergents, and to soften and improve the feel of cotton, comprise the above-mentioned endoglucanase component which possesses a high ability to bind and degrade cellulose. Moreover, cellulase preparations comprising a large amount of endoglucanase component are less costly to produce than complex mixtures of enzymes and can be used in smaller quantities to produce the desired cellulase cleaning and softening effects.

It is well known to those skilled in the art of enzymology, that the cellulase enzyme can contain a region that functions primarily to bind the cellulase enzyme to the cellulose substrate. Cellulases that contain this domain are identified as surface-active cellulases since they possess the ability to bind to the surface of textiles. Cellulases lacking this domain are designated as nonsurface-active cellulases since they cannot bind with the cellulose contained in textiles for any considerable length of time. The discovery of a particular combination of endoglucanases capable of enhancing cleaning and improving softening would permit the cost-effective production-of cellulase using recombinant deoxyribonucleic acid (DNA) methods.

It is further well known in the art that certain cellulases can produce negative effects on cotton garments, such as weight loss and tensile strength loss. These negative effects can be minimized by choosing a combination of surface-active and nonsurface active cellulases which results in an optimum length of contact with the garment. Similarly, these negative effects can be minimized by controlling the length of time the enzyme is active in the wash liquor.

Accordingly, despite the aforementioned disclosures in the art, the need exists for a detergent composition containing an enzymatic mixture comprising a specific combination surface-active and nonsurface-active endoglucanases which enhances the cleaning ability of laundry detergents and which softens and improves the feel of cotton. There is also a need for such a detergent composition which maintains colors and removes stains. Furthermore, despite the previously mentioned disclosures in the art, there still remains a need for such a detergent composition comprising a specific combination of surface-active and nonsurface-active cellulases that is capable of delivering enhanced cleaning, softening and color maintenance results without concomitant weight loss and tensile strength loss in cotton garments.

BACKGROUND ART

The following patents and publications disclose detergent compositions containing cellulase enzymes: Bjork et al, U.S. Pat. No. 5,120,463 (Genentech international, Inc.); Boyer et al, WO 93/11215 (The Procter & Gamble Company); Convents et al, U.S. Pat. No. 5,443,750 (The Procter & Gamble Company); Suzuki et al, U.S. Pat. No. 4,822,516 (Kao Corporation); Suzuki et al, U.S. Pat. No. 4,978,470 (Kao Corporation). The following patent discloses a cellulase preparation: Barbesgaard et al. U.S. Pat. No. 4,435,307 (Novo Industri A/S); Rasmussen et al, EP 0.531.372 (Novo Nordisk A/S).

SUMMARY OF THE INVENTION

The aforementioned needs in the art are met by the present invention which provides an optimum combination of cellulase enzymes containing endoglucanases, in a detergent composition, together which enhance the cleaning ability of laundry detergents and soften and improve the feel of cotton. Additionally, the laundry detergent composition of this invention includes a combination of cellulases which maintains colors and removes stains. Furthermore, the detergent composition comprising a combination of surface-active and nonsurface-active cellulases delivers enhanced cleaning, softening and color maintenance results without concomitant weight loss and tensile strength loss in cotton garments. The detergent composition, of the present invention, comprises a surfactant, builder and an enzymatic mixture, capable of degrading cellulose, comprising a combination of a surface-active and a nonsurface-active cellulases.

Accordingly, in its composition aspect the detergent composition comprises at least about 1% by weight of a surfactant and at least about 1% by weight of a builder. Additionally, the detergent composition contains an effective amount of an enzymatic mixture capable of degrading cellulose comprising a combination of at least two cellulases, of which one is a surface-active cellulase and one is a nonsurface-active cellulase. Preferably, the detergent composition comprises at least about 0.005% by weight of the enzymatic mixture. The nonsurface-active cellulase and the surface-active cellulase are in a weight ratio of from about 1:2 to about 20:1 in the detergent composition.

In accordance with another composition aspect, the present invention is directed to an enzymatic mixture comprising from about 0.01% to about 2% by weight of a surface-active cellulase and from about 0.02% to about 3% by weight of a nonsurface-active cellulase, with the balance being water. The nonsurface-active cellulase and the surface-active cellulase are in a weight ratio of from about 1:2 to about 20:1 in the enzymatic mixture.

In accordance with its method aspect, the present invention is directed to a method of laundering soiled fabrics comprising the step of contacting said fabrics with a detergent composition comprising a surfactant, builder and combination of enzymes. The laundering process is carried out in an aqueous laundering solution wherein from about 2,000 parts per million to about 10,000 parts per million of the detergent composition are present in the aqueous solution.

Accordingly, it is an object of the present invention to provide a combination of endoglucanases, in a detergent composition, which enhances the cleaning ability of laundry detergents and softens and improves the feel of cotton. It is also an object of the present invention to provide a detergent composition comprising a specific combination of cellulases which maintains and rejuvenates colors and removes stains. Furthermore, it is an object of the present invention to provide a detergent composition comprising a specific combination of surface-active and nonsurface-active cellulases which delivers enhanced cleaning, softening and color maintenance results without concomitant weight loss and tensile strength loss in cotton garments.

These and other objects, features and attendant advantages of the present invention will become apparent to those skilled in the art from reading the following detailed description of the preferred embodiment and the appended claims. All documents, including patents and publications cited herein, are incorporated by reference. As used herein, all percentages, proportions, and ratios are by weight unless otherwise specified.

DETAILED DESCRIPTION OF THE PREFERRED EMBODIMENT

The aforementioned needs in the art are met by the present invention which provides a detergent composition comprising an enzymatic mixture made up of a combination of cellulase enzymes containing endoglucanases which enhance the cleaning ability of the laundry detergent and soften and improve the feel of cotton. Additionally, the present invention provides a detergent composition which maintains and rejuvenates colors and removes stains. Furthermore, the detergent composition containing the combination of cellulases which delivers enhanced cleaning, softening and color maintenance results without concomitant weight loss and tensile strength loss in cotton garments.

As used herein, "cellobiohydrolase activity", refers to the activity toward cellobiose p-nitrophenyl. The activity is determined as $10^{-6}$ mole nitrophenyl released per minute at 37° C. and pH 7.0.

As used herein, "CMC-endoase activity", refers to the endoglucanase activity of the endoglucanase component in terms of its ability to degrade cellulose to glucose, cellobiose and triose, as determined by the decrease in viscosity of a solution of carboxymethyl cellulose after incubation with the cellulase preparation of the invention. One CMC-endoase unit is defined as the amount of enzyme which forms per minute an amount of reducing carbohydrate equivalent to $10^{-6}$ mole of glucose in a reaction conducted at pH 7.0, at a temperature of 40° C. and for 20 minutes. The CMC-endoase activity can be determined from the viscosity decrease of CMC, as follows: A substrate solution is prepared, containing 35 g/l CMC (Hercules 7 LFD) in 0.1M tris buffer at pH 9.0. The enzyme sample to be analyzed is dissolved in the same buffer. 10 ml substrate solution and 0.5 ml enzyme solution are mixed and transferred to a viscosimeter (e.g. Haake VT 181, NV sensor, 181 rpm), thermostated at 40° C. Viscosity readings are taken as soon as possible after mixing and again 30 minutes later. The amount of enzyme that reduces the viscosity to one half under these conditions is defined as 1 unit of CMC-endoase activity, or 1 Cellulase Equivalent Viscosity Unit (CEVU) per liter.

As used herein, "DNA sequence", refers to the sequence of nucleotide residues in the DNA molecule which code for a specific sequence of amino acids in the polypeptide chain of a type of protein. Each amino acid is coded for by three successive nucleotide residues in the DNA called a coding triplet.

As used herein, "endoglucanase enzyme", refers to all components of cellulase which exhibit endoglucanase type activity and which are a part of the cellulase system produced by a given microorganism. Endoglucanase enzymes hydrolyze soluble cellulose derivatives such as carboxymethyl cellulose (CMC), thereby reducing the viscosity of such solutions.

As used herein, "homologue", refers to a polypeptide encoded by DNA which hybridizes to the same probe as the DNA coding for the surface-active or nonsurface-active endoglucanase enzyme with this amino acid sequence under certain specified conditions (such as presoaking in 5×SSC and prehybridizing for 1 h at 40° C. in a solution of 20% formahide, 5×Denhardt's solution. 50 mM sodium phosphate, pH 6.8, and 50 $\mu$g of denatured sonicated calf thymus DNA, followed by hybridization in the same solution supplemented with 100 $\mu$M ATP for 18 h at 40° C.).

As used herein, "host cell", refers to the microorganism which is transformed with a recombinant DNA vector which carries a DNA sequence encoding for an endoglucanase enzyme.

As used herein, "isoelectric point", refers to the pH at which the positive and negative charges on the particles of a colloidal solution cancel each other so that the particles become electrically neutral.

As used herein, "nonsurface-active cellulase", refers to a cellulase enzyme which does not possess a cellulose binding domain and is not capable of binding with cellulose for an extended period to time.

As used herein, "recombinant DNA vector" refers to the system into which the DNA sequence encoding for the endoglucanase enzyme is inserted. The vector may be a plasmid (extrachromosomal entity which replicates independently of chromosomal replication) or may be one which, when introduced into a host cell, is integrated into the host cell genome and replicated together with the chromosome into which it has been integrated. The choice of vector will often depend on the host cell into which it is to be introduced.

As used herein, "surface-active cellulase", refers to a cellulase enzyme which possesses a cellulose binding domain and is capable of binding with cellulose for an extended period of time.

During the washing process, the surface active cellulase in the detergent formulation interacts with the cellulose on the surface of the textile fibers of the garments being washed whereby the cellulose/cellulase combination is then released into the wash liquor. As a result of this interaction, the binding site of this cellulase molecule is bound with the cellulose in solution and no longer free to return to the surface of the textile. The bound-up combination of the surface-active cellulase and cellulose remain in solution in the wash liquor during the washing process, thereby reducing the number of surface-active molecules available to return to the surface of the textile.

While not intending to be bound by theory, it is hypothesized that the nonsurface-active cellulase of the present invention functions by interacting with the cellulose bound to the surface-active cellulase, thereby allowing the surface-active cellulase to return to the surface of the textile where its binding site is free to interact with cellulose again. The number of molecules of surface-active cellulase contacting the fibers of a textile at any one is a function of the equilibrium between the surface-active and nonsurface-active cellulases. It is further hypothesized that the positive effects of the cellulase combination. such as enhanced cleaning and color maintenance, result from the combined celluloytic activity of the surface-active and nonsurface-active cellulases. The negative effects, such as weight loss and tensile strength loss result from too many cellulase molecules residing on the surface of the textile at any one time. The detergent composition of the invention described herein provides an unexpected reduction of the negative weight loss and tensile strength loss effects associated with cellulases without a diminution in the positive enhanced cleaning and color maintenance effects.

The level of surface-active and nonsurface-active cellulase described above should be such that the amount of total cellulase enzyme to be delivered in the wash solution is from about 0.005 to about 1.0 mg/liter of wash solution, preferably from about 0.01 to about 0.2 mg/liter of wash solution. The detergent composition of the present invention must include the aforementioned enzymatic mixture of surface-active and nonsurface-active cellulase enzymes as well as a builder and surfactant. Adjunct detergent ingredients optionally may be included in the detergent composition, as well. Nonlimiting examples of the surfactant, builder, cellulase, and preferred adjunct anti-redeposition agents, bleaching compounds, brighteners, chelating agents, dye transfer inhibiting agents, enzyme stabilizers, other adjunct ingredients, polymeric dispersion agents, polymeric soil release agents, softeners, and suds suppressors are described in detail hereinafter.

Surfactant

Nonlimiting examples of surfactants useful herein typically at levels of at least 1%, preferably from about 1% to about 55%, by weight, include the conventional $C_{11}$–$C_{18}$ alkyl benzene sulfonates ("LAS") and primary, branched-chain and random $C_{10}$–$C_{20}$ alkyl sulfates ("AS"), the $C_{10}$–$C_{18}$ secondary (2,3) alkyl sulfates of the formula $CH_3(CH_2)_x(CHOSO_3^-M^+)CH_3$ and $CH_3(CH_2)_y(CHOSO_3^-M^+)CH_2CH_3$ where x and (y+1) are integers of at least about 7, preferably at least about 9, and M is a water-solubilizing cation, especially sodium, unsaturated sulfates such as oleyl sulfate, the $C_{10}$–$C_{18}$ alkyl ethoxy sulfates ("$AE_xS$"; especially EO 1–7 ethoxy sulfates), $C_{10}$–$C_{18}$ alkyl ethoxy carboxylates (especially the EO 1–5 ethoxycarboxylates), the $C_{10-18}$ glycerol ethers, the $C_{10}$–$C_{18}$ alkyl polyglycosides and their corresponding sulfated polyglycosides, and $C_{12}$–$C_{18}$ alpha-sulfonated fatty acid esters. If desired, the conventional nonionic and amphoteric surfactants such as the $C_{12}$–$C_{18}$ alkyl ethoxylates ("AE") including the so-called narrow peaked alkyl ethoxylates and $C_6$–$C_{12}$ alkyl phenol alkoxylates (especially ethoxylates and mixed ethoxy/propoxy), $C_{12}$–$C_{18}$ betaines and sulfobetaines ("sultaines"), $C_{10}$–$C_{18}$ amine oxides, and the like, can also be included in the overall compositions. The $C_{10}$–$C_{18}$ N-alkyl polyhydroxy fatty acid amides can also be used. Typical examples include the $C_{12}$–$C_{18}$ N-methylglucamides. See WO 9,206,154. Other sugar-derived surfactants include the N-alkoxy polyhydroxy fatty acid amides, such as $C_{10}$–$C_{18}$ N-(3-methoxypropyl) glucamide. The N-propyl through N-hexyl $C_{12}$–$C_{18}$ glucamides can be used for low sudsing. $C_{10}$–$C_{20}$ conventional soaps may also be used. If high sudsing is desired, the branched-chain $C_{10}$–$C_{16}$ soaps may be used. Mixtures of anionic and nonionic surfactants are especially useful. Other conventional useful surfactants are listed in standard texts.

Builder

Detergent builders are included in the compositions herein, for example to assist in controlling mineral, especially Ca and/or Mg, hardness in wash water or to assist in the removal of particulate soils from surfaces. Builders can operate via a variety of mechanisms including forming soluble or insoluble complexes with hardness ions, by ion exchange, and by offering a surface more favorable to the precipitation of hardness ions than are the surfaces of articles to be cleaned. Builder level can vary widely depending upon end use and physical form of the composition. Built detergents typically comprise at least about 1% by weight of a builder. Liquid formulations typically comprise about 5% to about 50%, more typically 5% to 35% of builder. Granular formulations typically comprise from about 10% to about 80%, more typically 15% to 50% builder by weight of the detergent composition. Lower or higher levels of builders are not excluded. For example, certain detergent additive or high-surfactant formulations can be unbuilt.

Suitable builders herein can be selected from the group consisting of phosphates and polyphosphates, especially the sodium salts; silicates including water-soluble and hydrous solid types and including those having chain-, layer-, or three-dimensional-structure as well as amorphous-solid or non-structured-liquid types; carbonates, bicarbonates, sesquicarbonates and carbonate minerals other than sodium carbonate or sesquicarbonate; aluminosilicates; organic mono-, di-, tri-, and tetracarboxylates especially water-soluble nonsurfactant carboxylates in acid, sodium, potassium or alkanolammonium salt form, as well as oligomeric or water-soluble low molecular weight polymer carboxylates including aliphatic and aromatic types: and phytic acid. These may be complemented by borates, e.g., for pH-buffering purposes, or by sulfates, especially sodium sulfate and any other fillers or carriers which may be important to the engineering of stable surfactant and/or builder-containing detergent compositions.

Builder mixtures, sometimes termed "builder systems" can be used and typically comprise two or more conventional builders, optionally complemented by chelants, pH-buffers or fillers, though these latter materials are generally accounted for separately when describing quantities of materials herein. In terms of relative quantities of surfactant and builder in the present detergents, preferred builder systems are typically formulated at a weight ratio of surfactant to builder of from about about 60:1 to about 1:80. Certain preferred laundry detergents have said ratio in the range 0.90:1.0 to 4.0:1.0, more preferably from 0.95:1.0 to 3.0:1.0.

P-containing detergent builders often preferred where permitted by legislation include, but are not limited to, the alkali metal, ammonium and alkanolammonium salts of polyphosphates exemplified by the tripolyphosphates, pyrophosphates, glassy polymeric meta-phosphates; and phosphonates.

Suitable silicate builders include alkali metal silicates, particularly those liquids and solids having a $SiO_2:Na_2O$ ratio in the range 1.6:1 to 3.2:1, including, particularly for automatic dishwashing purposes, solid hydrous 2-ratio silicates marketed by PQ Corp. under the tradename BRITESIL®, e.g., BRITESIL H2O; and layered silicates, e.g., those described in U.S. Pat. No. 4,664,839, May 12, 1987, H. P. Rieck. NaSKS-6, sometimes abbreviated "SKS-6", is a crystalline layered aluminium-free $\delta$-$Na_2SiO_5$ morphology silicate marketed by Hoechst and is preferred especially in granular laundry compositions. See preparative methods in German DE-A-3,417,649 and DE-A-3,742,043. Other layered silicates, such as those having the general formula $NaMSi_xO_{2x+1}.yH_2O$ wherein M is sodium or hydrogen, x is a number from 1.9 to 4, preferably 2, and y is a number from 0 to 20, preferably 0, can also or alternately be used herein. Layered silicates from Hoechst also include NaSKS-5, NaSKS-7 and NaSKS-11, as the $\alpha$, $\beta$ and $\gamma$ layer-silicate forms. Other silicates may also be useful, such as magnesium silicate, which can serve as a crispening agent in granules, as a stabilising agent for bleaches, and as a component of suds control systems.

Also suitable for use herein are synthesized crystalline ion exchange materials or hydrates thereof having chain structure and a composition represented by the following general formula in an anhydride form: $xM_2O.ySiO_2.zM'O$ wherein M is Na and/or K, M' is Ca and/or Mg; y/x is 0.5 to 2.0 and z/x is 0.005 to 1.0 as taught in U.S. Pat. No. 5,427,711, Sakaguchi et al, Jun. 27, 1995.

Suitable carbonate builders include alkaline earth and alkali metal carbonates as disclosed in German Patent Application No. 2,321,001 published on Nov. 15, 1973, although sodium bicarbonate, sodium carbonate, sodium sesquicarbonate, and other carbonate minerals such as trona or any convenient multiple salts of sodium carbonate and calcium carbonate such as those having the composition $2Na_2CO_3.CaCO_3$ when anhydrous, and even calcium carbonates including calcite, aragonite and vaterite, especially forms having high surface areas relative to compact calcite may be useful, for example as seeds or for use in synthetic detergent bars.

Aluminosilicate builders are especially useful in granular detergents, but can also be incorporated in liquids, pastes or gels. Suitable for the present purposes are those having empirical formula: $[M_z(AlO_2)_z(SiO_2)_v].xH_2O$ wherein z and v are integers of at least 6, the molar ratio of z to v is in the range from 1.0 to 0.5, and x is an integer from 15 to 264. Aluminosilicates can be crystalline or amorphous, naturally-occurring or synthetically derived. An aluminosilicate production method is in U.S. Pat. No. 3,985,669, Krummel, et al, Oct. 12, 1976. Preferred synthetic crystalline aluminosilicate ion exchange materials are available as Zeolite A, Zeolite P (B), Zeolite X and, to whatever extent this differs from Zeolite P, the so-called Zeolite MAP. Natural types, including clinoptilolite, may be used. Zeolite A has the formula: $Na_{12}[(AlO_2)_{12}(SiO_2)_{12}].xH_2O$ wherein x is from 20 to 30, especially 27. Dehydrated zeolites (x=0–10) may also be used. Preferably, the aluminosilicate has a particle size of 0.1–10 microns in diameter.

Suitable organic detergent builders include polycarboxylate compounds, including water-soluble nonsurfactant dicarboxylates and tricarboxylates. More typically builder polycarboxylates have a plurality of carboxylate groups, preferably at least 3 carboxylates. Carboxylate builders can be formulated in acid, partially neutral, neutral or overbased form. When in salt form, alkali metals, such as sodium, potassium, and lithium, or alkanolammonium salts are preferred. Polycarboxylate builders include the ether polycarboxylates, such as oxydisuccinate, see Berg, U.S. Pat. No. 3,128,287, Apr. 7, 1964, and Lamberti et al, U.S. Pat. No. 3,635,830, Jan. 18, 1972; "TMS/TDS" builders of U.S. Pat. No. 4,663,071, Bush et al, May 5, 1987; and other ether carboxylates including cyclic and alicyclic compounds, such as those described in U.S. Pat. Nos. 3,923,679; 3,835,163; 4,158,635; 4,120,874 and 4,102,903.

Other suitable builders are the ether hydroxypolycarboxylates, copolymers of maleic anhydride with ethylene or vinyl methyl ether; 1,3,5-trihydroxy benzene-2,4,6-trisulphonic acid; carboxymethyloxysuccinic acid; the various alkali metal, ammonium and substituted ammonium salts of polyacetic acids such as ethylenediamine tetraacetic acid and nitrilotriacetic acid; as well as mellitic acid, succinic acid, polymaleic acid, benzene 1,3,5-tricarboxylic acid, carboxymethyloxysuccinic acid, and soluble salts thereof.

Citrates, e.g., citric acid and soluble salts thereof are important carboxylate builders e.g., for heavy duty liquid detergents, due to availability from renewable resources and biodegradability. Citrates can also be used in granular compositions, especially in combination with zeolite and/or layered silicates. Oxydisuccinates are also especially useful in such compositions and combinations.

Where permitted, and especially in the formulation of bars used for hand-laundering operations, alkali metal phosphates such as sodium tripolyphosphates, sodium pyrophosphate and sodium orthophosphate can be used. Phosphonate builders such as ethane-1-hydroxy-1,1-diphosphonate and other known phosphonates, e.g., those of U.S. Pat. Nos. 3,159,581; 3,213,030; 3,422,021; 3,400,148 and 3,422,137 can also be used and may have desirable antiscaling properties.

Certain detersive surfactants or their short-chain homologs also have a builder action. For unambiguous formula accounting purposes, when they have surfactant capability, these materials are summed up as detersive surfactants. Preferred types for builder functionality are illustrated by: 3,3-dicarboxy-4-oxa-1,6-hexanedioates and the related compounds disclosed in U.S. Pat. No. 4,566,984, Bush, Jan. 28, 1986. Succinic acid builders include the $C_5$–$C_{20}$ alkyl and alkenyl succinic acids and salts thereof. Succinate builders also include: laurylsuccinate, myristylsuccinate, palmitylsuccinate, 2-dodecenylsuccinate (preferred), 2-pentadecenylsuccinate, and the like. Laurylsuccinates are described in European Patent Application 86200690.5/0,200,263, published Nov. 5, 1986. Fatty acids, e.g., $C_{12}$–$C_{18}$ monocarboxylic acids, can also be incorporated into the compositions as surfactant/builder materials alone or in combination with the aforementioned builders, especially citrate and/or the succinate builders, to provide additional builder activity. Other suitable polycarboxylates are disclosed in U.S. Pat. No. 4,144,226, Crutchfield et al. Mar. 13, 1979 and in U.S. Pat. No. 3,308,067, Diehl, Mar. 7, 1967. See also Diehl, U.S. Pat. No. 3,723,322.

Optionally, inorganic builder materials can be used which have the formula $(M_x)_i\, Ca_y\, (CO_3)_z$ wherein x and i are integers from 1 to 15, y is an integer from 1 to 10, z is an integer from 2 to 25, $M_i$ are cations, at least one of which is a water-soluble, and the equation $\Sigma_{i=1\text{-}15}(x_i$ multiplied by the valence of $M_i)+2y=2z$ is satisfied such that the formula has a neutral or "balanced" charge. Waters of hydration or anions other than carbonate may be added provided that the overall charge is balanced or neutral. The charge or valence effects of such anions should be added to the right side of the above equation. Preferably, there is present a water-soluble cation selected from the group consisting of hydrogen, water-soluble metals, hydrogen, boron, ammonium, silicon, and mixtures thereof, more preferably, sodium, potassium, hydrogen, lithium, ammonium and mixtures thereof, sodium and potassium being highly preferred. Nonlimiting examples of noncarbonate anions include those selected from the group consisting of chloride, sulfate, fluoride, oxygen, hydroxide, silicon dioxide, chromate, nitrate, borate and mixtures thereof Preferred builders of this type in their simplest forms are selected from the group consisting of $Na_2Ca(CO_3)_2$, $K_2Ca(CO_3)_2$, $Na_2Ca_2(CO_3)_3$, $NaKCa_2(CO_3)_2$, $NaKCa_2Ca_2(CO_3)_3$, $K_2Ca_2(CO_3)_3$, and combinations thereof. An especially preferred material for the builder described herein is $Na_2Ca(CO_3)_2$ in any of its crystalline modifications. Suitable builders of the above-defined type are further illustrated by, and include, the natural or synthetic forms of any one or combinations of the following minerals: Afghanite, Andersonite, AshcroftineY, Beyerite, Borcarite, Burbankite, Butschliite, Cancrinite, Carbocernaite, Carietonite, Davyne, DonnayiteY, Fairchildite, Ferrisurite, Franzinite, Gaudefroyite, Gaylussite, Giryasite, Gregoryite, Jouravskite, KamphaugiteY, Kettnerite, Khanneshite, LepersonniteGd, Liottite, MckelveyiteY, Microsommite, Mroseite, Natrofairchildite, Nyerereite, RemonditeCe, Sacrofanite, Schrockingerite, Shortite, Surite, Tunisite, Tuscanite, Tyrolite, Vishnevite, and Zemkorite. Preferred mineral forms include Nyererite, Fairchildite and Shortite.

Cellulase

The amount of total cellulase (i.e., surface-active and nonsurface-active combined) used in the present invention is preferably from about 0.0001% to about 1.0% and more preferably from about 0.0002% to about 0.5%, by weight, of the detergent composition. Preferably, in the detergent composition, the surface-active cellulase provides from about 5% to about 67% and the nonsurface-active cellulase provides from about 33% to about 95% of the total cellulase activity in the enzymatic mixture. Preferably, the optimum pH of the total enzymatic mixture is between about 5 to about 10.5.

The detergent composition described herein comprises a surface-active cellulase which is an endoglucanase enzyme having the amino acid sequence shown in the Sequence Listing as SEQ ID NO:2 or a homologue thereof exhibiting endoglucanase activity, and produced by species of Humicola such as *Humicola insolens* e.g., strain DS 1800, deposited on Oct. 1, 1981 at the Deutsche Sammlung von Mikroorganismen, Mascheroder Weg 1B, D-3300 Braunschweig, FRG, in accordance with the provisions of the Budapest Treaty on the International Recognition of the Deposit of Microorganisms for the Purposes of Patent Procedure. U.S. Pat. No. 4,435,307, Barbesgaard et al, issued Mar. 6, 1984, discloses cellulase produced from Humicola insolens. Examples of other suitable cellulases include those produced by a strain of *Humicola insolens, Humicola grisea* var *thermoidea*, and cellulases produced by a species of Bacillus sp. or Aeromonas sp. Other useful cellulases are those extracted from the hepatopancreas of the marine mollusc Dolabella Auricula Solander.

Suitable cellulases are also disclosed in the following: GB 2,075,028 A (Novo Industri A/S); GB 2,095,275 A (Kao Soap Co., Ltd.); and Horikoshi et al, U.S. Pat. No. 3,844,890 (Rikagaku Kenkyusho). In addition, suitable cellulases and methods for their preparation are described in PCT International Publication Number WO 91/17243, published Nov. 14, 1991, by Novo Nordisk A/S.

In another preferred aspect of the present invention, the detergent composition described herein comprises a surface-active cellulase which is an endoglucanase enzyme having the amino acid sequence shown in the Sequence Listing as SEQ ID NO:4 and produced by species of Fusarium such as *Fusarium oxysporum*, e.g., strain DSM 2672, deposited on Jun. 6, 1983 at the Deutsche Sammlung von Mikroorganismen, Mascheroder Weg 1B, D-3300 Braunschweig, FRG, in accordance with the provisions of the Budapest Treaty on the International Recognition of the Deposit of Microorganisms for the Purposes of Patent Procedure.

In another preferred aspect of the present invention, the detergent composition described herein contains a surface-active cellulase which comprises a homogeneous endoglucanase enzyme with activity of at least 50 CMC-endoase units per milligram of total protein. The isoelectric point of the endoglucanase of the surface-active cellulase is 5.1. Isoelectric focusing with marker proteins, in a manner known to persons skilled in the art, was used to determine the isoelectric point of the endoglucanase component of the surface-active cellulase preparation useful in the present context. Additionally, the detergent composition of the present invention preferably comprises an endoglucanase enzyme of the surface-active cellulase which is substantially free of cellobiohydrolase activity.

In another preferred aspect of the present invention, the detergent composition described herein contains a nonsurface-active cellulase which comprises a homogeneous endoglucanase enzyme with activity of at least 50 CMC-endoase units per milligram of total protein. The isoelectric point of the endoglucanase of the nonsurface-active cellulase is 5.1. Isoelectric focusing with marker proteins, in a manner known to persons skilled in the art, was used to determine the isoelectric point of the endoglucanase component of the nonsurface-active cellulase preparation useful in the present context. Additionally, the detergent composition of the present invention preferably comprises an endoglulase enzyme of the nonsurface-active cellulase which is substantially free of cellobiohydrolase activity.

Recombinant DNA Techniques

For industrial production of the surface-active and nonsurface-active cellulases of the enzymatic mixture described herein it is preferred that recombinant DNA techniques be employed. However, other techniques involving adjustments of fermentations or mutation of the microorganisms involved can be employed to ensure overproduction of the desired enzymatic activities. Such methods and techniques are known in the art and may readily be carried out by persons skilled in the art.

The surface-active endoglucanase enzyme produced by Humicola and having the amino acid sequence shown in Sequence Listing SEQ ID NO:2 and the surface-active endoglucanase enzyme produced by Fusarium and having the amino acid sequence shown in Sequence Listing SEQ ID NO:4. may thus be ones which are produced by recombinant DNA methods. Additionally, the nonsurface-active endoglucanase enzyme having the amino acid sequence shown in Sequence Listing SEQ ID NO:6 and the nonsurface-active endoglucanase enzyme having the amino acid sequence shown in Sequence Listing SEQ ID NO:8 may also be ones which are produce by recombinant DNA methods.

Specifically, all of the endoglucanases described above may be produced by a method comprising cultivating a host cell transformed with a recombinant DNA vector carrying a DNA sequence encoding the endoglucanase enzyme, or a precursor of the endoglucanase enzyme of either the surface-active or nonsurface-active cellulase. In addition, it may be necessary to transform a host cell with a recombinant DNA vector carrying DNA sequences encoding functions permitting the expression of the DNA sequence encoding the endoglucanases. The host cell is cultivated in a suitable culture medium and under conditions permitting the expression of the surface-active and nonsurface-active endoglucanase enzymes, or their precursors.

Shown in Sequence Listing SEQ ID NO:1 is the DNA sequence encoding the endoglucanase enzyme of the surface-active cellulase produced by Humicola and the cellulase having the amino acid sequence shown in Sequence Listing SEQ ID NO:2, both of which are identical. Shown in Sequence Listing SEQ ID NO:3, is the DNA sequence encoding the endoglucanase enzyme of the surface-active cellulase produced by Fusarium and the endoglucanase enzyme having the amino acid sequence shown in Sequence Listing SEQ ID NO:4, both of which are identical.

Sequence Listing SEQ ID NO:5 is the DNA sequence encoding the endoglucanase enzyme of the nonsurface-active cellulase has the amino acid sequence shown in Sequence Listing SEQ ID NO:6. The DNA sequence encoding the endoglucanase enzyme of the nonsurface-active cellulase having the amino acid sequence shown in Sequence Listing SEQ ID NO:8, is as shown in Sequence Listing SEQ ID NO:7. Suitable modifications of the DNA sequence encoding any of the surface-active and nonsurface-active endoglucanases are possible.

Examples of suitable modifications of the DNA sequence are nucleotide substitutions which do not give rise to another amino acid sequence of the endoglucanase, but which correspond to the codon usage of the host organism into which the DNA sequence encoding the surface-active or nonsurface-active endoglucanase enzyme is introduced. In addition, nucleotide substitutions which do give rise to a different amino acid sequence and therefore, possibly, a different protein structure which might give rise to an endoglucanase mutant with different properties other than the native enzyme may also be suitable modifications of the DNA sequence. Other examples of possible modifications are insertion of one or more nucleotides at either end of the sequence, or deletion of one or more nucleotides at either end or within the sequence.

DNA sequences encoding endoglucanase enzymes useful herein may be prepared synthetically by established standard methods, e.g. the phosphoamidite method described by S. L. Beaucage and M. H. Caruthers, *Tetrahedron Letters* 22, 1981, pp. 1859–1869, or the method described by Matthes et al., *EMBO Journal* 3, 1984, pp. 801–805. According to the phosphoamidite method, oligonucleotides are synthesized, e.g. in an automatic DNA synthesizer, purified, annealed, ligated and cloned in suitable vectors.

A DNA sequence encoding the surface-active or nonsurface-active endoglucanase enzyme or a precursor thereof may, for instance, be isolated by establishing a complementary DNA (cDNA) or genomic library of a cellulase-producing microorganism, such as Humicola isolens, DSM 1800, and screening for positive clones by conventional procedures such as by hybridization using oligonucleotide probes synthesized on the basis of the full or partial amino acid sequence of the endoglucanase in accordance with standard techniques (e.g., Sambrook et al., *Molecular Cloning: A Laboratory Manual*, 2nd Ed. Cold Spring Harbor, 1989), or by selecting for clones expressing the appropriate enzyme activity (i.e. CMC-endoase activity as defined above), or by selecting for clones producing a protein which is reactive with an antibody against a native cellulase (endoglucanase).

Finally, the DNA sequence encoding the surface-active or nonsurface active endoglucanase enzyme may be of mixed synthetic and genomic, mixed synthetic and cDNA or mixed genomic and cDNA origin prepared by ligating fragments of synthetic, genomic or cDNA origin (as appropriate), the fragments corresponding to various parts of the entire DNA construct, in accordance with standard techniques. The DNA sequence encoding the surface-active or nonsurface-active endoglucanase enzyme may also be prepared by polymerase chain reaction using specific primers, for instance as described in Mullis, U.S. Pat. No. 4,683,202 (Cetus Corporation) or R. K. Saiki et al., *Science* 239, 1988, pp. 487–491.

Recombinant expression vectors into which the above DNA sequence encoding the surface-active or nonsurface-active endoglucanase enzymes are inserted include any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

In the vector, the DNA sequence encoding the surface-active or nonsurface-active endoglucanase enzymes should be operably connected to a suitable promoter and terminator sequence. The promoter may be any DNA sequence which shows transcriptional activity in the host cell of choice and may be derived from genes encoding proteins either homologous or heterologous to the host cell. The procedures used to ligate the DNA sequences coding for the surface-active or nonsurface-active endoglucanase enzymes, the promoter and the terminator, respectively, and to insert them into suitable vectors are well known to persons skilled in the art (cf., for instance, Sambrook et al., al., op.cit.).

Host cells which are transformed with the above DNA sequences encoding for any of the above-mentioned surface-active and nonsurface-active endoglucanase enzymes may be any microorganism selected from the group consisting of the genera Aspergillus, Trichoderma, Hansenula, Saccharomyces, Streptomyces, Bacillus and Eschericia. Fungal cells may be transformed by a process involving protoplast formation and transformation of the protoplasts followed by regeneration of the cell wall. The use of Aspergillus as a host microorganism is described in EP 238, 023 (of Novo Nordisk A/S). If the host cell is a bacterial cell, transformation may be performed according to conventional methods, (cf., for instance, Sambrook et al., op.cit.). The screening of appropriate DNA sequences and construction of vectors may also be carried out by standard procedures, (cf. Sambrook et al., op.cit.).

The medium used to cultivate the transformed host cells may be any conventional medium suitable for growing the host cells in question. The expressed endoglucanase may conveniently be secreted into the culture medium and may be recovered therefrom by well-known procedures including separating the cells from the medium by centrifugation or filtration, precipitating proteinaceous components of the medium by means of a salt such as ammonium sulfate, followed by chromatographic procedures such as ion exchange chromatography, affinity chromatography, or the like.

By employing recombinant DNA techniques as indicated above, techniques of protein purification, techniques of fermentation and mutation or other techniques which are well known in the art, it is possible to provide surface-active and nonsurface-active endoglucanases suitable for incorporation in the detergent composition of the instant invention of a high purity.

Adjunct Ingredients

The compositions herein can optionally include one or more other detergent adjunct materials or other materials for assisting or enhancing cleaning performance, treatment of the substrate to be cleaned, or to modify the aesthetics of the detergent composition (e.g., perfumes, colorants, dyes. etc.). The following are illustrative examples of anti-redeposition agents, bleaching compounds, brighteners, chelating agents, dye transfer inhibiting agents, enzyme stabilizers, other adjunct ingredients, polymeric dispersion agents, polymeric soil release agents, softeners and suds suppressors.

Anti-redeposition Agents

The compositions of the present invention can also optionally contain water-soluble ethoxylated amines having clay soil removal and anti-redeposition properties. Granular detergent compositions which contain these compounds typically contain from about 0.01% to about 10.0% by weight of the water-soluble ethoxylates amines; liquid detergent compositions typically contain about 0.01% to about 5.0%.

The most preferred soil release and anti-redeposition agent is ethoxylated tetraethylenepentamine. Exemplary ethoxylated amines are further described in U.S. Pat. No. 4,597,898, VanderMeer, issued Jul. 1, 1986. Another group of preferred clay soil removal-anti-redeposition agents are the cationic compounds disclosed in European Patent Application 111,965, Oh and Gosselink, published Jun. 27, 1984. Other clay soil removal/anti-redeposition agents which can be used include the ethoxylated amine polymers disclosed in European Patent Application 111,984, Gosselink, published Jun. 27, 1984; the zwitterionic polymers disclosed in European Patent Application 112,592, Gosselink, published Jul. 4, 1984; and the amine oxides disclosed in U.S. Pat. No. 4,548,744, Connor, issued Oct. 22, 1985. Other clay soil removal and/or anti-redeposition agents known in the art can also be utilized in the compositions herein. Another type of preferred anti-redeposition agent includes the carboxymethyl cellulose materials. These materials are well known in the art.

Bleaching Compounds

The detergent compositions herein may optionally contain bleaching agents or bleaching compositions containing a bleaching agent and one or more bleach activators. When present, bleaching agents will typically be at levels of from about 1% to about 30%, more typically from about 5% to about 20%, of the detergent composition, especially for fabric laundering. If present, the amount of bleach activators will typically be from about 0.1% to about 60%, more typically from about 0.5% to about 40% of the bleaching composition comprising the bleaching agent-plus-bleach activator.

The bleaching agents used herein can be any of the bleaching agents useful for detergent compositions in textile cleaning, hard surface cleaning, or other cleaning purposes that are now known or become known. These include oxygen bleaches as well as other bleaching agents. Perborate bleaches, e.g., sodium perborate (e.g., mono- or tetra-hydrate) can be used herein.

Another category of bleaching agent that can be used without restriction encompasses percarboxylic acid bleaching agents and salts thereof. Suitable examples of this class of agents include magnesium monoperoxyphthalate hexahydrate, the magnesium salt of metachloro perbenzoic acid, 4-nonylamino-4-oxoperoxybutyric acid and diperoxy-dodecanedioic acid. Such bleaching agents are disclosed in U.S. Pat. No. 4,483,781, Hartman, issued Nov. 20, 1984, U.S. patent application Ser. No. 740,446, Burns et al, filed Jun. 3, 1985, European Patent Application 0,133,354, Banks et al, published Feb. 20, 1985, and U.S. Pat. No. 4,412,934, Chung et al, issued Nov. 1, 1983. Highly preferred bleaching agents also include 6-nonylamino-6-oxoperoxycaproic acid as described in U.S. Pat. No. 4,634,551, issued Jan. 6, 1987 to Burns et al.

Peroxygen bleaching agents can also be used. Suitable peroxygen bleaching compounds include sodium carbonate peroxyhydrate and equivalent "percarbonate" bleaches, sodium pyrophosphate peroxyhydrate, urea peroxyhydrate, and sodium peroxide. Persulfate bleach (e.g., OXONE®, manufactured commercially by DuPont) can also be used.

A preferred percarbonate bleach comprises dry particles having an average particle size in the range from about 500 micrometers to about 1,000 micrometers, not more than about 10% by weight of the particles being smaller than about 200 micrometers and not more than about 10% by weight of the particles being larger than about 1,250 micrometers. Optionally, the percarbonate can be coated with silicate, borate or water-soluble surfactants. Percarbonate is available from various commercial sources such as FMC, Solvay and Tokai Denka. Mixtures of bleaching agents can also be used.

Peroxygen bleaching agents, the perborates, the percarbonates, etc., are preferably combined with bleach activators, which lead to the in situ production in aqueous solution (i.e., during the washing process) of the peroxy acid corresponding to the bleach activator. Various nonlimiting examples of activators are disclosed in U.S. Pat. No. 4,915, 854, issued Apr. 10, 1990 to Mao et al, and U.S. Pat. No. 4,412,934. The nonanoyloxybenzene sulfonate (NOBS) and tetraacetyl ethylene diamine (TAED) activators are typical, and mixtures thereof can also be used. See also U.S. Pat. No. 4,634,551 for other typical bleaches and activators useful herein.

Highly preferred amido-derived bleach activators are those of the formulae:

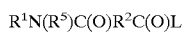

or

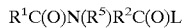

wherein $R^1$ is an alkyl group containing from about 6 to about 12 carbon atoms, $R^2$ is an alkylene containing from 1 to about 6 carbon atoms, $R^5$ is H or alkyl, aryl, or alkaryl containing from about 1 to about 10 carbon atoms, and L is any suitable leaving group. A leaving group is any group that is displaced from the bleach activator as a consequence of the nucleophilic attack on the bleach activator by the perhydrolysis anion. A preferred leaving group is phenyl sulfonate.

Preferred examples of bleach activators of the above formulae include (6-octanamido-caproyl) oxybenzenesulfonate, (6-nonanamidocaproyl) oxybenzenesulfonate, (6-decanamido-caproyl) oxybenzenesulfonate, and mixtures thereof as described in U.S. Pat. No. 4,634,551, incorporated herein by reference.

Another class of bleach activators comprises the benzoxazin-type activators disclosed by Hodge et al in U.S. Pat. No. 4,966,723, issued Oct. 30, 1990, incorporated herein by reference. A highly preferred activator of the benzoxazin-type is:

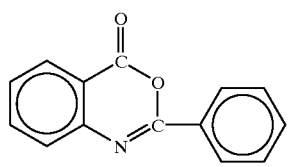

Still another class of preferred bleach activators includes the acyl lactam activators, especially acyl caprolactams and acyl valerolactams of the formulae:

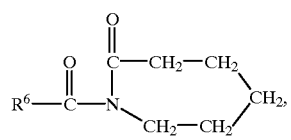

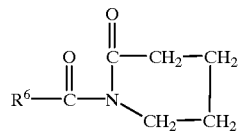

wherein $R^6$ is H or an alkyl, aryl, alkoxyaryl, or alkaryl group containing from 1 to about 12 carbon atoms. Highly preferred lactam activators include benzoyl caprolactam, octanoyl caprolactam, 3,5,5-trimethylhexanoyl caprolactam, nonanoyl caprolactam, decanoyl caprolactam, undecenoyl caprolactam, benzoyl valerolactam, octanoyl valerolactam, decanoyl valerolactam, undecenoyl valerolactam, nonanoyl valerolactam, 3,5,5-trimethylhexanoyl valerolactam and mixtures thereof. See also U.S. Pat. No. 4,545,784, issued to Sanderson, Oct. 8, 1985, incorporated herein by reference, which discloses acyl caprolactams, including benzoyl caprolactam, adsorbed into sodium perborate.

Bleaching agents other than oxygen bleaching agents are also known in the art and can be utilized herein. One type of non-oxygen bleaching agent of particular interest includes photoactivated bleaching agents such as the sulfonated zinc and/or aluminum phthalocyanines. See U.S. Pat. No. 4,033, 718, issued Jul. 5, 1977 to Holcombe et al. If used, detergent compositions will typically contain from about 0.025% to about 1.25%, by weight, of such bleaches, especially sulfonate zinc phthalocyanine.

If desired, the bleaching compounds can be catalyzed by means of a manganese compound. Such compounds are well known in the art and include, for example, the manganese-based catalysts disclosed in U.S. Pat. Nos. 5,246,621, 5,244, 594; 5,194,416; 5,114,606; and European Pat. App. Pub. Nos. 549,271A1, 549,272A1, 544,440A2, and 544,490A1; Preferred examples of these catalysts include $Mn^{IV}{}_2(u\text{-}O)_3$ $(1,4,7\text{-trimethyl-}1,4,7\text{-triazacyclononane})_2(PF_6)_2$, $Mn^{III}{}_2(u\text{-}O)_1(u\text{-}OAc)_2(1,4,7\text{-trimethyl-}1,4,7\text{-triazacyclononane})_2\text{-}(ClO_4)_2$, $Mn^{IV}{}_4(u\text{-}O)_6(1,4,7\text{-triazacyclononane})_4(ClO_4)_4$, $Mn^{III}Mn^{IV}{}_4(u\text{-}O)_1(u\text{-}OAc)_2\text{-}(1,4,7\text{-trimethyl-}1,4,7\text{-triazacyclononane})_2(ClO_4)_3$, $Mn^{IV}(1,4,7\text{-trimethyl-}1,4,7\text{-triazacyclononane})\text{-}(OCH_3)_3(PF_6)$, and mixtures thereof. Other metal-based bleach catalysts include those disclosed in U.S. Pat. Nos. 4,430,243 and 5,114,611. The use of manganese with various complex ligands to enhance bleaching is also reported in the following U.S. Pat. Nos.: 4,728, 455; 5,284,944; 5,246,612; 5,256,779; 5,280,117; 5,274, 147; 5,153,161; and 5,227,084.

As a practical matter, and not by way of limitation, the compositions and processes herein can be adjusted to provide on the order of at least one part per ten million of the active bleach catalyst species in the aqueous washing liquor, and will preferably provide from about 0.1 ppm to about 700 ppm, more preferably from about 1 ppm to about 500 ppm, of the catalyst species in the laundry liquor.

Any optical brighteners or other brightening or whitening agents known in the art can be incorporated at levels typically from about 0.05% to about 1.2%, by weight, into the detergent compositions herein. Commercial optical brighteners which may be useful in the present invention can be classified into subgroups, which include, but are not necessarily limited to, derivatives of stilbene, pyrazoline, coumarin, carboxylic acid, methinecyanines, dibenzothiphene-5,5-dioxide, azoles, 5- and 6-membered-ring heterocycles, and other miscellaneous agents. Examples of such brighteners are disclosed in "The Production and Application of Fluorescent Brightening Agents", M. Zahradnik. Published by John Wiley & Sons, New York (1982).

Specific examples of optical brighteners which are useful in the present compositions are those identified in U.S. Pat. No. 4,790,856. issued to Wixon on Dec. 13, 1988. These brighteners include the PHORWHITE® series of brighteners from Verona. Other brighteners disclosed in this reference include: Tinopal UNPA®, Tinopal CBS® and Tinopal 5BM®; available from Ciba-Geigy; Artic White CC™ and Artic White CWD™, available from Hilton-Davis, located in Italy; the 2-(4-stryl-phenyl)-2H-napthol[1,2-d]triazoles; 4,4'-bis-(1,2,3-triazol-2-yl)-stil-benes; 4,4'-bis(stryl) bisphenyls; and the aminocoumarins. Specific examples of these brighteners include 4-methyl-7-diethyl-amino coumarin; 1,2-bis(-venzimidazol-2-yl)ethylene; 1,3-diphenyl-phrazolines; 2,5-bis(benzoxazol-2-yl)thiophene: 2-stryl-napth-[1,2-d]oxazole; and 2-(stilbene-4-yl)-2H-naphtho-[1, 2-d]triazole. See also U.S. Pat. No. 3,646,015, issued Feb. 29, 1972 to Hamilton. Anionic brighteners are preferred herein.

Chelating Agents

The detergent compositions herein may also optionally contain one or more iron and/or manganese chelating agents. Such chelating agents can be selected from the group consisting of amino carboxylates, amino phosphonates, polyfunctionally-substituted aromatic chelating agents and mixtures therein, all as hereinafter defined. Without intending to be bound by theory, it is believed that the benefit of these materials is due in part to their exceptional ability to remove iron and manganese ions from washing solutions by formation of soluble chelates.

Amino carboxylates useful as optional chelating agents include ethylenediaminetetracetates, N-hydroxyethylethylenediaminetriacetates, nitrilotriacetates, ethylenediamine tetraproprionates, triethylenetetraaminehexacetates, diethylenetriaminepentaacetates, and ethanoldiglycines, alkali metal, ammonium, and substituted ammonium salts therein and mixtures therein.

Amino phosphonates are also suitable for use as chelating agents in the compositions of the invention when at lease low levels of total phosphorus are permitted in detergent compositions, and include ethylenediaminetetrakis (methylenephosphonates) as DEQUEST®. Preferred, these amino phosphonates to not contain alkyl or alkenyl groups with more than about 6 carbon atoms.

Polyfunctionally-substituted aromatic chelating agents are also useful in the compositions herein. See U.S. Pat. No. 3,812,044, issued May 21, 1974, to Connor et al. Preferred compounds of this type in acid form are dihydroxydisulfobenzenes such as 1,2-dihydroxy-3,5-disulfobenzene.

A preferred biodegradable chelator for use herein is ethylenediamine disuccinate ("EDDS"), especially the [S,S] isomer as described in U.S. Pat. No. 4,704,233, Nov. 3, 1987, to Hartman and Perkins.

If utilized, these chelating agents will generally comprise from about 0.1% to about 10% by weight of the detergent compositions herein. More preferably, if utilized, the chelating agents will comprise from about 0.1% to about 3.0% by weight of such compositions.

Dye Transfer Inhibiting Agents

The compositions of the present invention may also include one or more materials effective for inhibiting the transfer of dyes from one fabric to another during the cleaning process. Generally, such dye transfer inhibiting agents include polyvinyl pyrrolidone polymers, polyamine N-oxide polymers, copolymers of N-vinylpyrrolidone and N-vinylimidazole, manganese phthalocyanine, peroxidases, and mixtures thereof. If used, these agents typically comprise from about 0.01% to about 10% by weight of the composition, preferably from about 0.01% to about 5%, and more preferably from about 0.05% to about 2%.

More specifically, the polyamine N-oxide polymers preferred for use herein contain units having the following structural formula: R—A$_x$—P; wherein P is a polymerizable unit to which an N—O group can be attached or the N—O group can form part of the polymerizable unit or the N—O group can be attached to both units; A is one of the following structures: —NC(O), —C(O)O—, —S—, —O—, —N=; x is 0 or 1; and R is aliphatic, ethoxylated aliphatics, aromatics, heterocyclic or alicyclic groups or any combination thereof to which the nitrogen of the N—O group can be attached or the N—O group is part of these groups. Preferred polyamine N-oxides are those wherein R is a heterocyclic group such as pyridine, pyrrole, imidazole, pyrrolidine, piperidine and derivatives thereof.

The N—O group can be represented by the following general structures:

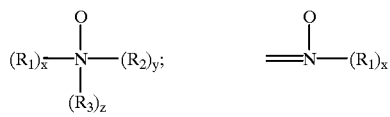

wherein $R_1$, $R_2$, $R_3$ are aliphatic, aromatic, heterocyclic or alicyclic groups or combinations thereof, x, y and z are 0 or 1; and the nitrogen of the N—O group can be attached or form part of any of the aforementioned groups. The amine oxide unit of the polyamine N-oxides has a pKa <10, preferably pKa <7, more preferred pKa <6.

Any polymer backbone can be used as long as the amine oxide polymer formed is water-soluble and has dye transfer inhibiting properties. Examples of suitable polymeric backbones are polyvinyls, polyalkylenes, polyesters, polyethers, polyamide, polyimides, polyacrylates and mixtures thereof. These polymers include random or block copolymers where one monomer type is an amine N-oxide and the other monomer type is an N-oxide.

The amine N-oxide polymers typically have a ratio of amine to the amine N-oxide of 10:1 to 1:1,000,000. However, the number of amine oxide groups present in the polyamine oxide polymer can be varied by appropriate copolymerization or by an appropriate degree of N-oxidation. The polyamine oxides can be obtained in almost any degree of polymerization. Typically, the average molecular weight is within the range of 500 to 1,000,000; more preferred 1,000 to 500,000; most preferred 5,000 to 100,000.

The most preferred polyamine N-oxide useful in the detergent compositions herein is poly(4-vinylpyridine-N-oxide) which as an average molecular weight of about 50,000 and an amine to amine N-oxide ratio of about 1:4. This preferred class of materials can be referred to as "PVNO".

Copolymers of N-vinylpyrrolidone and N-vinylimidazole polymers (referred to as a class as "PVPVI") are also preferred for use herein. Preferably the PVPVI has an average molecular weight range from 5,000 to 1,000,000, more preferably from 5,000 to 200,000, and most preferably from 10,000 to 20,000. (The average molecular weight range is determined by light scattering as described in Barth, et al., *Chemical Analysis*, Vol 113. "Modern Methods of Polymer Characterization", the disclosures of which are incorporated herein by reference.) The PVPVI copolymers typically have a molar ratio of N-vinylimidazole to N-vinylpyrrolidone from 1:1 to 0.2:1, more preferably from 0.8:1 to 0.3:1, most preferably from 0.6:1 to 0.4:1. These copolymers can be either linear or branched.

The present invention compositions also may employ a polyvinylpyrrolidone ("PVP") having an average molecular weight of from about 5,000 to about 400,000, preferably from about 5,000 to about 200,000, and more preferably from about 5,000 to about 50,000. PVP's are known to persons skilled in the detergent field; see, for example, EP-A-262,897 and EP-A-256,696, incorporated herein by reference. Compositions containing PVP can also contain polyethylene glycol ("PEG") having an average molecular weight from about 500 to about 100,000, preferably from about 1,000 to about 10,000. Preferably, the ratio of PEG to PVP on a ppm basis delivered in wash solutions is from about 2:1 to about 50:1, and more preferably from about 3:1 to about 10:1.

The detergent compositions herein may also optionally contain from about 0.005% to 5% by weight of certain types of hydrophilic optical brighteners which also provide a dye transfer inhibition action. If used, the compositions herein will preferably comprise from about 0.01% to 1% by weight of such optical brighteners.

The hydrophilic optical brighteners useful in the present invention are those having the structural formula:

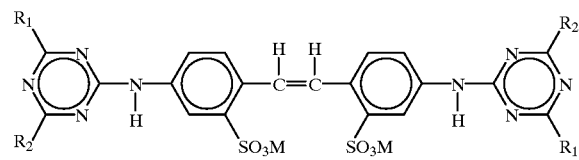

wherein $R_1$ is selected from anilino, N-2-bis-hydroxyethyl and NH-2-hydroxyethyl; $R_2$ is selected from N-2-bis-hydroxyethyl, N-2-hydroxyethyl-N-methylamino, morpholino, chloro and amino; and M is a salt-forming cation such as sodium or potassium.

When in the above formula, $R_1$ is anilino, $R_2$ is N-2-bis-hydroxyethyl and M is a cation such as sodium, the brightener is 4,4',-bis[(4-anilino-6-(N-2-bis-hydroxyethyl)-s-triazine-2-yl)amino]-2,2'-stilbenedisulfonic acid and disodium salt. This particular brightener species is commercially marketed under the tradename Tinopal-UNPA-GX® by Ciba-Geigy Corporation. Tinopal-UNPA-GX is the preferred hydrophilic optical brightener useful in the detergent compositions herein.

When in the above formula, $R_1$ is anilino, $R_2$ is N-2-hydroxyethyl-N-2-methylamino and M is a cation such as sodium, the brightener is 4,4'-bis[(4-anilino-6-(N-2-hydroxyethyl-N-methylamino)-s-triazine-2-yl)amino]2,2'-stilbenedisulfonic acid disodium salt. This particular brightener species is commercially marketed under the tradename Tinopal 5BM-GX® by Ciba-Geigy Corporation.

When in the above formula, $R_1$ is anilino, $R_2$ is morpholino and M is a cation such as sodium, the brightener is 4,4'-bis[(4-anilino-6-morpholino-s-triazine-2-yl)amino]2,2'-stilbenedisulfonic acid, sodium salt. This particular brightener species is commercially marketed under the tradename Tinopal AMS-GX® by Ciba Geigy Corporation.

The specific optical brightener species selected for use in the present invention provide especially effective dye transfer inhibition performance benefits when used in combination with the selected polymeric dye transfer inhibiting agents hereinbefore described. The combination of such selected polymeric materials (e.g., PVNO and/or PVPVI) with such selected optical brighteners (e.g., Tinopal UNPA-GX®, Tinopal 5BM-GX® and/or Tinopal AMS-GX®) provides significantly better dye transfer inhibition in aqueous wash solutions than does either of these two detergent composition components when used alone. Without being bound by theory, it is believed that such brighteners work this way because they have high affinity for fabrics in the wash solution and therefore deposit relatively quick on these fabrics. The extent to which brighteners deposit on fabrics in the wash solution can be defined by a parameter called the "exhaustion coefficient". The exhaustion coefficient is in general as the ratio of: a) the brightener material deposited on fabric; to b) the initial brightener concentration in the wash liquor. Brighteners with relatively high exhaustion coefficients are the most suitable for inhibiting dye transfer in the context of the present invention.

Of course, it will be appreciated that other, conventional optical brightener types of compounds can optionally be used in the present compositions to provide conventional fabric "brightness" benefits, rather than a true dye transfer inhibiting effect. Such usage is conventional and well-known to detergent formulations.

Enzyme Stabilizers

The enzymes employed herein optionally can be stabilized by the presence of water-soluble sources of calcium and/or magnesium ions in the finished compositions which provide such ions to the enzymes. Calcium ions are generally somewhat more effective than magnesium ions and are preferred herein if only one type of cation is being used. Additional stability can be provided by the presence of various other art-disclosed stabilizers, especially borate species: see Severson, U.S. Pat. No. 4,537,706. Typical detergents, especially liquids, will comprise from about 1 to about 30, preferably from about 2 to about 20, more preferably from about 5 to about 15, and most preferably from about 8 to about 12, millimoles of calcium ion per liter of finished composition. This can vary somewhat, depending on the amount of enzyme present and its response to the calcium or magnesium ions. The level of calcium or magnesium ions should be selected so that there is always some minimum level available for the enzyme, after allowing for complexation with builders, fatty acids, and other components in the composition. Any water-soluble calcium or magnesium salt can be used as the source of calcium or magnesium ions, including, but not limited to, calcium chloride, calcium sulfate, calcium malate, calcium maleate, calcium hydroxide, calcium formate, and calcium acetate, and the corresponding magnesium salts. A small amount of calcium ion, generally from about 0.05 to about 0.4 millimoles per liter, is often also present in the composition due to calcium in the enzyme slurry and formula water. In solid detergent compositions the formulation may include a sufficient quantity of a water-soluble calcium ion source to provide such amounts in the laundry liquor. In the alternative, natural water hardness may suffice.

It is to be understood that the foregoing levels of calcium and/or magnesium ions are sufficient to provide enzyme stability. More calcium and/or magnesium ions can be added to the compositions to provide an additional measure of grease removal performance. Accordingly, as a general proposition the compositions herein will typically comprise from about 0.05% to about 2% by weight of a water-soluble source of calcium or magnesium ions, or both. The amount can vary, of course, with the amount and type of enzyme employed in the composition.

The compositions herein may also optionally, but preferably, contain various additional stabilizers, especially borate-type stabilizers. Typically, such stabilizers will be used at levels in the compositions from about 0.25% to about 10%, preferably from about 0.5% to about 5%, more preferably from about 0.75% to about 3%, by weight of boric acid or other borate compound capable of forming boric acid in the composition (calculated on the basis of boric acid). Boric acid is preferred, although other compounds such as boric oxide, borax and other alkali metal borates (e.g., sodium ortho-, meta- and pyroborate, and sodium pentaborate) are suitable. Substituted boric acids (e.g., phenylboronic acid, butane boronic acid, and p-bromo phenylboronic acid) can also be used in place of boric acid.

Other Adjunct Ingredients

A wide variety of other ingredients useful in detergent compositions can be included in the compositions herein, including other active ingredients, carriers, hydrotropes, processing aids, dyes or pigments, solvents for liquid formulations, solid fillers for bar compositions, etc. If high sudsing is desired, suds boosters such as the $C_{10}$–$C_{16}$ alkanolamides can be incorporated into the compositions, typically at 1%–10% levels. The $C_{10}$–$C_{14}$ monoethanol and diethanol amides illustrate a typical class of such suds boosters. Use of such suds boosters with high sudsing adjunct surfactants such as the amine oxides, betaines and sultaines noted above is also advantageous. If desired, soluble magnesium salts such as $MgCl_2$, $MgSO_4$, and the like, can be added at levels of, typically, 0.1%–2%, to provide additional suds and to enhance grease removal performance.

Various detersive ingredients employed in the present compositions optionally can be further stabilized by absorbing the ingredients onto a porous hydrophobic substrate and then coating the substrate with a hydrophobic coating. Preferably, the detersive ingredient is admixed with a surfactant before being absorbed into the porous substrate. In use, the detersive ingredient is released from the substrate into the aqueous washing liquor, where it performs its intended detersive function.

To illustrate this technique in more detail, a porous hydrophobic silica (trademark SIPERNAT DI®, DeGussa) is admixed with a proteolytic enzyme solution containing 3%–5% of $C_{13-15}$ ethoxylated alcohol (EO 7) nonionic surfactant. Typically, the enzyme/surfactant solution is 2.5× the weight of silica. The resulting powder is dispersed with stirring in silicone oil (various silicone oil viscosities in the range of 500–12,500 can be used). The resulting silicone oil dispersion is emulsified or otherwise added to the final detergent matrix. By this means, ingredients such as the aforementioned enzymes, bleaches, bleach activators, bleach catalysts, photoactivators, dyes, fluorescers, fabric conditioners and hydrolyzable surfactants can be "protected" for use in detergents, including liquid laundry detergent compositions.

Liquid detergent compositions can contain water and other solvents as carriers. Low molecular weight primary or secondary alcohols exemplified by methanol, ethanol, propanol, and isopropanol are suitable. Monohydric alcohols are preferred for solubilizing surfactant, but polyols such as those containing from 2 to about 6 carbon atoms and from 2 to about 6 hydroxy groups (e.g., 1,3-propanediol, ethylene glycol, glycerine, and 1,2-propanediol) can also be used. The compositions may contain from 5% to 90%, typically 10% to 50% of such carriers.

The detergent compositions herein will preferably be formulated such that, during use in aqueous cleaning operations, the wash water will have a pH of between about 6.5 and about 11, preferably between about 7.5 and 10.5. Liquid dishwashing product formulations preferably have a pH between about 6.8 and about 9.0. Laundry products are typically at pH 9–11. Techniques for controlling pH at recommended usage levels include the use of buffers, alkalis, acids, etc., and are well known to those skilled in the art.

Polymeric Dispersion Agents

Polymeric dispersing agents can advantageously be utilized at levels from about 0.1% to about 7%, by weight, in the compositions herein, especially in the presence of zeolite and/or layered silicate builders. Suitable polymeric dispersing agents include polymeric polycarboxylates and polyethylene glycols, although others known in the art can also be used. It is believed, though it is not intended to be limited by theory, that polymeric dispersing agents enhance overall detergent builder performance, when used in combination with other builders (including lower molecular weight polycarboxylates) by crystal growth inhibition, particulate soil release peptization, and anti-redeposition.

Polymeric polycarboxylate materials can be prepared by polymerizing or copolymerizing suitable unsaturated monomers, preferably in their acid form. Unsaturated monomeric acids that can be polymerized to form suitable polymeric polycarboxylates include acrylic acid, maleic acid (or maleic anhydride), fumaric acid, itaconic acid, aconitic acid, mesaconic acid, citraconic acid and methylenemalonic acid. The presence in the polymeric polycarboxylates herein or monomeric segments, containing no carboxylate radicals such as vinylmethyl ether, styrene, ethylene, etc. is suitable provided that such segments do not constitute more than about 40% by weight.

Particularly suitable polymeric polycarboxylates can be derived from acrylic acid Such acrylic acid-based polymers which are useful herein are the water-soluble salts of polymerized acrylic acid. The average molecular weight of such polymers in the acid form preferably ranges from about 2,000 to 10,000, more preferably from about 4,000 to 7,000 and most preferably from about 4,000 to 5,000. Water-soluble salts of such acrylic acid polymers can include, for example, the alkali metal, ammonium and substituted ammonium salts. Soluble polymers of this type are known materials. Use of polyacrylates of this type in detergent compositions has been disclosed, for example. in Diehl. U.S. Pat. No. 3,308,067. issued Mar. 7, 1967.

Acrylic/maleic-based copolymers may also be used as a preferred component of the dispersing/anti-redeposition agent. Such materials include the water-soluble salts of copolymers of acrylic acid and maleic acid. The average molecular weight of such copolymers in the acid form preferably ranges from about 2,000 to 100,000. more preferably from about 5,000 to 75,000, most preferably from about 7,000 to 65,000. The ratio of acrylate to maleate segments in such copolymers will generally range from about 30:1 to about 1:1. more preferably from about 10:1 to 2:1. Water-soluble salts of such acrylic acid/maleic acid copolymers can include, for example, the alkali metal, ammonium and substituted ammonium salts. Soluble acrylate/maleate copolymers of this type are known materials which are described in European Patent Application No. 66915, published Dec. 15, 1982, as well as in EP 193,360, published Sep. 3, 1986, which also describes such polymers comprising hydroxypropylacrylate. Still other useful dispersing agents include the maleic/acrylic/vinyl alcohol terpolymers. Such materials are also disclosed in EP 193,360, including, for example, the 45/45/10 terpolymer of acrylic/maleic/vinyl alcohol.

Another polymeric material which can be included is polyethylene glycol (PEG).

PEG can exhibit dispersing agent performance as well as act as a clay soil removal-antiredeposition agent. Typical molecular weight ranges for these purposes range from about 500 to about 100,000, preferably from about 1,000 to about 50,000, more preferably from about 1,500 to about 10,000. Polyaspartate and polyglutamate dispersing agents may also be used, especially in conjunction with zeolite builders. Dispersing agents such as polyaspartate preferably have an average molecular weight of about 10,000.

Polymeric Soil Release Agents

Any polymeric soil release agent known to those skilled in the art can optionally be employed in the compositions and processes of this invention. Polymeric soil release agents are characterized by having both hydrophilic segments, to hydrophilize the surface of hydrophobic fibers, such as polyester and nylon, and hydrophobic segments, to deposit upon hydrophobic fibers and remain adhered thereto through completion of washing and rinsing cycles and thus, serve as an anchor for the hydrophilic segments. This can enable stains occurring subsequent to treatment with the soil release agent to be more easily cleaned in later washing procedures.

The polymeric soil release agents useful herein especially include those soil release agents having: (a) one or more nonionic hydrophile components consisting essentially of (i) polyoxyethylene segments with a degree of polymerization of at least 2, or (ii) oxypropylene or polyoxypropylene segments with a degree of polymerization of from 2 to 10, wherein said hydrophile segment does not encompass any oxypropylene unit unless it is bonded to adjacent moieties at each end by ether linkages, or (iii) a mixture of oxyalkylene units comprising oxyethylene and from 1 to about 30 oxypropylene units wherein said mixture contains a sufficient amount of oxyethylene units such that the hydrophile component has hydrophilicity great enough to increase the hydrophilicity of conventional polyester synthetic fiber surfaces upon deposit of the soil release agent on such surface, said hydrophile segments preferably comprising at least about 25% oxyethylene units and more preferably, especially for such components having about 20 to 30 oxypropylene units, at least about 50% oxyethylene units; or (b) one or more hydrophobe components comprising (i) $C_3$ oxyalkylene terephthalate segments, wherein, if said hydrophobe components also comprise oxyethylene terephthalate, the ratio of oxyethylene terephthalate:$C_3$ oxyalkylene terephthalate units is about 2:1 or lower, (ii) $C_4$–$C_6$ alkylene or oxy $C_4$–$C_6$ alkylene segments, or mixtures therein, (iii) poly (vinyl ester) segments, preferably polyvinyl acetate), having a degree of polymerization of at least 2, or (iv) $C_1$–$C_4$ alkyl ether or $C_4$ hydroxyalkyl ether substituents, or mixtures therein, wherein said substituents are present in the form of $C_1$–$C_4$ alkyl ether or $C_4$ hydroxyalkyl ether cellulose derivatives, or mixtures therein, and such cellulose derivatives are amphiphilic, whereby they have a sufficient level of $C_1$–$C_4$ alkyl ether and/or $C_4$ hydroxyalkyl ether units to deposit upon conventional polyester synthetic fiber surfaces and retain a sufficient level of hydroxyls, once adhered to such conventional synthetic fiber surface, to increase fiber surface hydrophilicity, or a combination of (a) and (b).

Typically, the polyoxyethylene segments of (a)(i) will have a degree of polymerization of from about 200, although higher levels can be used, preferably from 3 to about 150, more preferably from 6 to about 100. Suitable oxy $C_4$–$C_6$ alkylene hydrophobe segments include, but are not limited to, end-caps of polymeric soil release agents such as $MO_3S$ $(CH_2)_nOCH_2CH_2O$—, where M is sodium and n is an integer from 4–6, as disclosed in U.S. Pat. No. 4,721,580, issued Jan. 26, 1988 to Gosselink.

Polymeric soil release agents useful in the present invention also include cellulosic derivatives such as hydroxyether cellulosic polymers, copolymeric blocks of ethylene terephthalate or propylene terephthalate with polyethylene oxide or polypropylene oxide terephthalate, and the like. Such agents are commercially available and include hydroxyethers of cellulose such as METHOCEL® (Dow). Cellulosic soil release agents for use herein also include those selected from the group consisting of $C_1$–$C_4$ alkyl and $C_4$ hydroxyalkyl cellulose; see U.S. Pat. No. 4,000,093, issued Dec. 28, 1976 to Nicol et al.

Soil release agents characterized by poly(vinyl ester) hydrophobe segments include graft copolymers of poly (vinyl ester), e.g., $C_1$–$C_6$ vinyl esters, preferably poly(vinyl acetate) grafted onto polyalkylene oxide backbones, such as polyethylene oxide backbones. See European Patent Application 0 219 048, published Apr. 22. 1987 by Kud et al. Commercially available soil release agents of this kind include the SOKALAN® type of material, e.g., SOKALAN® HP-22. available from BASF (West Germany).

One type of preferred soil release agent is a copolymer having random blocks of ethylene terephthalate and polyethylene oxide (PEO) terephthalate. The molecular weight of this polymeric soil release agent is in the range of from about 25,000 to about 55,000. See U.S. Pat. No. 3,959,230 to Hays, issued May 25, 1976 and U.S. Pat. No. 3,893,929 to Basadur issued Jul. 8, 1975.

Another preferred polymeric soil release agent is a polyester with repeat units of ethylene terephthalate units contains 10–15% by weight of ethylene terephthalate units together with 90–80% by weight of polyoxyethylene terephthalate units, derived from a polyoxyethylene glycol of average molecular weight 300–5,000. Examples of this polymer include the commercially available material ZELCON® 5126 (from Dupont) and MILEASE T® (from ICI). See also U.S. Pat. No. 4,702,857, issued Oct. 27, 1987 to Gosselink.

Another preferred polymeric soil release agent is a sulfonated product of a substantially linear ester oligomer comprised of an oligomeric ester backbone of terephthaloyl and oxyalkyleneoxy repeat units and terminal moieties covalently attached to the backbone. These soil release agents are described fully in U.S. Pat. No. 4,968,451, issued Nov. 6, 1990 to J. J. Scheibel and E. P. Gosselink. Other suitable polymeric soil release agents include the terephthalate polyesters of U.S. Pat. No. 4,711,730, issued Dec. 8, 1987 to Gosselink et al, the anionic end-capped oligomeric esters of U.S. Pat. No. 4,721,580, issued Jan. 26, 1988 to Gosselink, and the block polyester oligomeric compounds of U.S. Pat. No. 4,702,857, issued Oct. 27, 1987 to Gosselink.

Preferred polymeric soil release agents also include the soil release agents of U.S. Pat. No. 4,877.896, issued Oct. 31, 1989 to Maldonado et al. which discloses anionic, especially sulfoarolyl, end-capped terephthalate esters. If utilized, soil release agents will generally comprise from about 0.01% to about 10.0%, by weight, of the detergent compositions herein, typically from about 0.1% to about 5%, preferably from about 0.2% to about 3.0%.

Still another preferred soil release agent is an oligomer with repeat units of terephthaloyl units, sulfoisoterephthaloyl units, oxyethyleneoxy and oxy-1.2-propylene units. The repeat units form the backbone of the oligomer and are preferably terminated with modified isethionate end-caps. A particularly preferred soil release agent of this type comprises about one sulfoisophthaloyl unit, 5 terephthaloyl units, oxyethyleneoxy and oxy-1,2-propyleneoxy units in a ratio of from about 1.7 to about 1.8, and two end-cap units of sodium 2-(2-hydroxyethoxy)-ethanesulfonate. The soil release agent also comprises from about 0.5% to about 20%, by weight of the oligomer, of a crystalline-reducing stabilizer, preferably selected from the group consisting of xylene sulfonate, cumene sulfonate, toluene sulfonate, and mixtures thereof.

Softeners

Various through-the-wash fabric softeners, especially the impalpable smectite clays of U.S. Pat. No. 4,062,647, Storm and Nirschl, issued Dec. 13, 1977, as well as other softener clays known in the art, can optionally be used typically at levels of from about 0.5% to about 10% by weight in the present compositions to provide fabric softener benefits concurrently with fabric cleaning. Clay softeners can be used in combination with amine and cationic softeners as disclosed, for example, in U.S. Pat. No. 375,416, Crisp et al, Mar. 1, 1983 and U.S. Pat. No. 4,291,071, Harris et al, issued Sep. 22, 1981.

Suds Suppressors

Compounds for reducing or suppressing the formation of suds optionally can be incorporated into the compositions of the present invention. Suds suppression can be of particular importance in the so-called "high concentration cleaning process" as described in U.S. Pat. Nos. 4,489,455 and 4,489,574 and in front-loading European-style washing machines.

A wide variety of materials may be used as suds suppressors, and suds suppressors are well known to those skilled in the art. See, for example, Kirk Othmer Encyclopedia of Chemical Technology, Third Edition, Volume 7, pages 430–447 (John Wiley & Sons, Inc., 1979). One category of suds suppressor of particular interest encompasses monocarboxylic fatty acid and soluble salts therein. See U.S. Pat. No. 2,954,347, issued Sep. 27, 1960 to Wayne St. John. The monocarboxylic fatty acids and salts thereof used as suds suppressor typically have hydrocarbyl chains of 10 to about 24 carbon atoms, preferably 12 to 18 carbon atoms. Suitable salts include the alkali metal salts such as sodium, potassium, and lithium salts, and ammonium and alkanolammonium salts.

The detergent compositions herein may also contain non-surfactant suds suppressors. These include, for example: high molecular weight hydrocarbons such as paraffin, fatty acid esters (e.g., fatty acid triglycerides), fatty acid esters of monovalent alcohols, aliphatic $C_{18}$–$C_{40}$ ketones (e.g., stearone), etc. Other suds inhibitors include N-alkylated amino triazines such as tri- to hexa-alkylmelamines or di- to tetra-alkyldiamine chlortriazines formed as products of cyanuric chloride with two or three moles of a primary or secondary amine containing 1 to 24 carbon atoms, propylene oxide, and monostearyl phosphates such as monostearyl alcohol phosphate ester and monostearyl di-alkali metal (e.g., K, Na, and Li) phosphates and phosphate esters. The hydrocarbons such as paraffin and haloparaffin can be utilized in liquid form. The liquid hydrocarbons will be liquid at room temperature and atmospheric pressure, and will have a pour point in the range of about −40° C. and about 50° C., and a minimum boiling point not less than about 110° C. (atmospheric pressure). It is also known to utilize waxy hydrocarbons, preferably having a melting point below about 100° C. The hydrocarbons constitute a preferred category of suds suppressor for detergent compositions. Hydrocarbon suds suppressors are described, for example, in U.S. Pat. No. 4,265,779, issued May 5, 1981 to Gandolfo et al. The hydrocarbons, thus, include aliphatic, alicyclic, aromatic, and heterocyclic saturated or unsaturated hydrocarbons having from about 12 to about 70 carbon atoms. The term "paraffin," as used in this suds suppressor discussion, is intended to include mixtures of true paraffins and cyclic hydrocarbons.

Another preferred category of non-surfactant suds suppressors comprises silicone suds suppressors. This category includes the use of polyorganosiloxane oils, such as polydimethylsiloxane, dispersions or emulsions of polyorganosiloxane oils or resins, and combinations of polyorganosiloxane with silica particles wherein the polyorganosiloxane is chemisorbed or fused onto the silica. Silicone suds suppressors are well known in the art and are, for example, disclosed in U.S. Pat. No. 4,265,779, issued May 5, 1981 to Gandolfo et al and European Patent Application No. 89307851.9, published Feb. 7, 1990, by Starch, M. S.

Other silicone suds suppressors are disclosed in U.S. Pat. No. 3,455,839 which relates to compositions and processes for defoaming aqueous solutions by incorporating therein small amounts of polydimethylsiloxane fluids.

Mixtures of silicone and silanated silica are described, for instance, in German Patent Application DOS 2,124,526. Silicone defoamers and suds controlling agents in granular detergent compositions are disclosed in U.S. Pat. No. 3.933,672. Bartolotta et al, and in U.S. Pat. No. 4,652,392, Baginski et al, issued Mar. 24, 1987.

An exemplary silicone based suds suppressor for use herein is a suds suppressing mount of a suds controlling agent consisting essentially of:

(1) polydimethylsiloxane fluid having a viscosity of from about 20 centistokes (cs) to about 1,500 cs. at 25° C.;

(2) from about 5 to about 50 parts per 100 parts by weight of siloxane resin composed of $(CH_3)_3SiO_{1/2}$ units of $SiO_2$ units in a ratio of from $(CH_3)_3$ $SiO_{1/2}$ units and to $SiO_2$ units of from about 0.6:1 to about 1.2:1; and (3) from about 1 to about 20 parts per 100 parts by weight of(i) of a solid silica gel.

In the preferred silicone suds suppressor used herein, the solvent for a continuous phase is made up of certain polyethylene glycols or polyethylene-polypropylene glycol copolymers or mixtures thereof, or polypropylene glycol. The primary silicone suds suppressor is branched/crosslinked and preferably not linear.

To illustrate this point further, typical liquid laundry detergent compositions with controlled suds will optionally comprise from about 0.001 to about 1, preferably from about 0.01 to about 0.7, most preferably from about 0.05 to about 0.5, weight percent of said silicone suds suppressor, which comprises (1) a nonaqueous emulsion of a primary antifoam agent which is a mixture of: (a) a polyorganosiloxane; (b) a resinous siloxane or a silicone resin-producing silicone compound; (c) a finely divided filler material; and (d) a catalyst to promote the reaction of mixture components (a), (b) and (c), to form silanolates;

(2) at least one nonionic silicone surfactant; and (3) polyethylene glycol or a copolymer of polyethylene-polypropylene glycol having a solubility in water at room temperature of more than about 2 weight percent; and without polypropylene glycol.

Similar amounts can be used in granular compositions, gels, etc. See also U.S. Pat. No. 4,978,471, Starch, issued Dec. 18, 1990; U.S. Pat. No. 4,983,316, Starch, issued Jan. 8, 1991; U.S. Pat. No. 5,288,431, Huber et al., issued Feb. 22, 1994; and U.S. Pat. Nos. 4,639,489 and 4,749,740, Aizawa et al at column 1, line 46 through column 4, line 35.

The silicone suds suppressor herein preferably comprises polyethylene glycol and a copolymer of polyethylene glycol/polypropylene glycol, all having an average molecular weight of less than about 1,000, preferably between about 100 and 800. The polyethylene glycol and polyethylene/polypropylene copolymers herein have a solubility in water at room temperature of more than about 2 percent of the composition by weight, preferably more than about 5 percent of the composition by weight.

The preferred solvent herein is polyethylene glycol having an average molecular weight of less than about 1,000, more preferably between about 100 and 800, most preferably between 200 and 400, and a copolymer of polyethylene glycol/polypropylene glycol, preferably PPG 200/PEG 300. Preferred is a weight ratio of between about 1:1 and 1:10, most preferably between 1:3 and 1:6, of polyethylene glycol:copolymer of polyethylene-polypropylene glycol.

The preferred silicone suds suppressors used herein do not contain polypropylene glycol, particularly of 4,000 molecular weight. They also preferably do not contain block copolymers of ethylene oxide and propylene oxide, like PLURONIC L101®.

Other suds suppressors useful herein comprise the secondary alcohols (e.g., 2-alkyl alkanols) and mixtures of such alcohols with silicone oils, such as the silicones disclosed in U.S. Pat. Nos. 4,798,679, 4,075,118 and EP 150,872. The secondary alcohols include the $C_6$–$C_{16}$ alkyl alcohols having a $C_1$–$C_{16}$ chain. A preferred alcohol is 2-butyl octanol, which is available from Condea under the trademark ISOFOL 12®. Mixtures of secondary alcohols are available under the trademark ISALCHEM 123® from Enichem. Mixed suds suppressors typically comprise mixtures of alcohol+silicone at a weight ratio of 1:5 to 5:1.

For any detergent compositions to be used in automatic laundry washing machines, suds should not form to the extent that they overflow the washing machine. Suds suppressors, when utilized, are preferably present in a "suds suppressing amount". By "suds suppressing amount" is meant that the formulator of the composition can select an amount of this suds controlling agent that will sufficiently control the suds to result in a low-sudsing laundry detergent for use in automatic laundry washing machines.

The compositions herein will generally comprise from 0% to about 5% of suds suppressor. When utilized as suds suppressors, monocarboxylic fatty acids, and salts therein, will be present typically in amounts up to about 5%, by weight, of the detergent composition. Preferably, from about 0.5% to about 3% of fatty monocarboxylate suds suppressor is utilized. Silicone suds suppressors are typically utilized in amounts up to about 2.0%, by weight, of the detergent composition, although higher amounts may be used. This upper limit is practical in nature, due primarily to concern with keeping costs minimized and effectiveness of lower amounts for effectively controlling sudsing. Preferably from about 0.01% to about 1% of silicone suds suppressor is used, more preferably from about 0.25% to about 0.5%. As used herein, these weight percentage values include any silica that may be utilized in combination with polyorganosiloxane, as well as any adjunct materials that may be utilized. Monostearyl phosphate suds suppressors are generally utilized in amounts ranging from about 0.1% to about 2%, by weight, of the composition. Hydrocarbon suds suppressors are typically utilized in amounts ranging from about 0.01% to about 5.0%, although higher levels can be used. The alcohol suds suppressors are typically used at 0.2%–3% by weight of the finished compositions.

Detergent Composition Formulation

The detergent compositions according to the present invention can be in the form of a granule, an agglomerate or a liquid. Preferably, the detergent composition is in the form of granules, agglomerates or mixtures thereof. Compositions according to the present invention, depending on whether they are liquid or granular, can be made by a variety of methods including liquid mixing according to a temperature and pH time profile, melting, dissolving, dry mixing, spray drying, agglomeration and granulation and combinations of any of these techniques. The preferred method of making granular detergent compositions, particularly those having a high density (compact) form involves a combination of spray drying, agglomeration in a high speed mixer and dry mixing. The base granule is prepared by a conventional spray drying process in which the starting ingredients are formed into a slurry and passed though a spray drying tower having a countercurrent stream of hot air (200–300° C.) resulting in the formation of porous granules.

Specifically, the process for making the granule starts with a first granular component containing a relatively insoluble anionic surfactant which is spray dried. Part of the spray dried product is diverted and subjected to a low level of nonionic surfactant spray-on before being reblended with the remainder. A second granular component is made by dry neutralization of an anionic surfactant using sodium carbonate as the neutralizing agent in a continuous high speed blender such as a Lödige KM mixer. The first and second components together with other dry mix ingredients such as the carboxylate chelating agent, inorganic peroxygen bleach, bleach activator, soil suspension agent, silicate and the polycarboxylate polymer and enzyme are then fed to a conveyor belt from which they are transferred to a horizontally rotating drum in which perfume and silicone suds suppressor are sprayed-on to the product. In highly preferred compositions, a further drum mixing step is employed in which a low (approximately 2%) level of finely divided crystalline aluminosilicate is introduced to increase density and improve granular flow characteristics.

Optionally, a portion of the detergent ingredients can be in the form of agglomerates and admixed. By way of example, the agglomerates are formed from two feed streams of various starting detergent ingredients which are continuously fed, at a rate of 1400 kg/hr, into a Lödige CB-30 mixer/densifier, one of which comprises a surfactant paste containing surfactant and water and the other stream containing starting dry detergent material containing aluminosilicate and sodium carbonate. The rotational speed of the shaft in the Lödige CB-30 mixer/densifier is about 1400 rpm and the median residence time is about 5–10 seconds. The contents from the Lödige CB-30 mixer/densifier are continuously fed into a Lödige KM-600 mixer/densifier for further agglomeration during which the mean residence time is about 6 minutes. The resulting detergent agglomerates are then fed to a fluid bed dryer and to a fluid bed cooler before being admixed with the spray dried granules. The remaining adjunct detergent ingredients are sprayed on or dry added to the blend of agglomerates and granules. See Capeci et al, U.S. Pat. Nos. 5,366,652; 5,486,303; 5,489,392; and 5,516,448.

Liquid detergent compositions can be prepared by admixing the essential and optional ingredients thereof in any desired order to provide compositions containing components in the requisite concentrations. Liquid compositions according to the present invention can also be in "compact form", useful for pretreating soiled fabrics prior to washing. In such case, the liquid detergent compositions according to the present invention will contain a lower amount of water, compared to conventional liquid detergents. For a preferred method of making the liquid detergent compositions according to the present invention, it has been found that liquid detergent compositions are advantageously prepared when pH and temperature are always kept constant or are reduced during production of the liquid detergent.

In order to make the present invention more readily understood, reference is made to the following examples, which are intended to be illustrative only and not intended to be limiting in scope.

EXAMPLES I–II

Several liquid detergent compositions are prepared as follows:

| Component | (% Weight) | |
|---|---|---|
| | I | II |
| $C_{14-15}$ alkyl ethoxylate sulfate (6.5) | 14.9 | 16.9 |
| $C_{12-13}$ alkyl ethoxlylate (6.5) | 0.8 | 2.0 |
| $C_{12-14}$ alkyl N-methyl glucamide | 5.0 | 3.2 |
| Monoethanolamine | 2.3 | 3.5 |
| Sodium formate | 0.2 | 0.3 |
| Calcium formate | 0.1 | 0.1 |
| Ethanol | 3.6 | 3.6 |
| Sodium tartrate mono- and di-succinate (80:20) | 3.1 | 2.1 |
| Brightener | 0.1 | 0.1 |
| 1,2 propane diol | 10.0 | 10.0 |
| Citric acid | 2.9 | 2.6 |
| Ethoxylated tetraethylenepentaimine | 1.1 | 1.1 |
| Protease | 0.6 | 0.5 |
| Cellulase enzyme mixture | 0.5 | 0.2 |
| Water and miscellaneous ingredients | 54.8 | 53.8 |
| TOTAL | 100.0 | 100.0 |

EXAMPLES III–IV

Several granular detergent compositions are prepared as follows:

| Component | (% Weight) | |
|---|---|---|
| Base Granule | III | IV |
| $C_{12-13}$ linear alkyl benzene sulfonate ("LAS") | 4.3 | 6.7 |
| $C_{14-15}$ alkyl sulfate ("AS") | 4.1 | 2.5 |
| $C_{14-15}$ alkyl ethoxylate sulfate (EO = 0.35) | 1.6 | 2.6 |
| Aluminosilicate | 13.7 | 19.1 |
| Sodium carbonate | 12.1 | 22.8 |
| Sodium sulfate | 5.5 | 5.7 |
| Sodium silicate (1.6r) | 0.6 | 0.6 |
| Polyacrylate, Na (MW = 4500) | 2.5 | 3.2 |
| Polyethylene glycol (MW = 4000) | 1.1 | 1.4 |
| Miscellaneous (water, brighteners, etc.) | 5.0 | 5.0 |
| Agglomerates | 39.0 | 20.0 |
| Admix/Spray-on | | |
| Sodium carbonate | 6.2 | 6.2 |
| Sodium perborate | 1.0 | 1.0 |
| Soil release polymer[1] | 0.4 | 0.0 |
| Suds suppressor[2] | 0.2 | 0.2 |
| Lipase enzyme | 0.2 | 0.2 |
| Protease enzyme | 0.3 | 0.3 |
| Cellulase enzyme | 0.3 | 0.3 |
| Nonionic[3] | 1.5 | 1.8 |
| Perfume | 0.4 | 0.4 |
| TOTAL | 100.0 | 100.0 |

[1]Sodium terephthalate sulfoisophthalate polymer which is an oligomer comprising about one sulfoisophthaloyl unit, 5 terephthaloyl units, oxyethyleneoxy and oxy-1,2-propyleneoxy units in a ratio of from about 1.7 to about 1.8, and two end-cap units of sodium 2-(2-hydroxyethoxy)-ethanesulfonate.
[2]Polydimethylsiloxane with trimethylsilyl end blocking units available from Dow Corning, Inc.
[3]Alkyl ethoxylate commercially available from Shell Chemical Company under the trademark NEODOL ® (23-9).

The base granule is produced by mixing the noted components into an aqueous slurry (e.g., in a crutcher) and spray drying the slurry in a conventional counter current spray drying tower. The agglomerates are made via the process described in U.S. Pat. Nos. 5,486,303 and 5,366,652, both to Capeci et al. The composition of the agglomerates is AS/LAS (75:25 wt. ratio at 30% by weight), sodium carbonate (21%), aluminosilicate (35%), water and other minor (balance). The present invention meets the aforementioned needs in the art by providing a combination of endoglucanases, in a detergent composition, which unexpectedly enhances the cleaning ability of laundry detergents and softens and improves the feel of cotton.

SEQUENCE LISTING

<160> NUMBER OF SEQ ID NOS: 8

<210> SEQ ID NO 1
<211> LENGTH: 1060
<212> TYPE: DNA
<213> ORGANISM: Humicola insolens
<220> FEATURE:
<221> NAME/KEY: CDS
<222> LOCATION: (10)..(924)
<220> FEATURE:
<221> NAME/KEY: mat_peptide
<222> LOCATION: (73)..(924)
<220> FEATURE:
<221> NAME/KEY: sig_peptide
<222> LOCATION: (10)..(72)

<400> SEQUENCE: 1

```
ggatccaag atg cgt tcc tcc ccc ctc ctc ccg tcc gcc gtt gtg gcc gcc        51
          Met Arg Ser Ser Pro Leu Leu Pro Ser Ala Val Val Ala Ala
              -20             -15                 -10 ctg ccg gtg ttg gcc ctt gcc gct gat ggc agg tcc acc cgc tac tgg         99
Leu Pro Val Leu Ala Leu Ala Ala Asp Gly Arg Ser Thr Arg Tyr Trp
        -5              -1   1               5 gac tgc tgc aag cct tcg tgc ggc tgg gcc aag aag gct ccc gtg aac        147
Asp Cys Cys Lys Pro Ser Cys Gly Trp Ala Lys Lys Ala Pro Val Asn
 10              15                  20                  25 cag cct gtc ttt tcc tgc aac gcc aac ttc cag cgt atc acg gac ttc        195
Gln Pro Val Phe Ser Cys Asn Ala Asn Phe Gln Arg Ile Thr Asp Phe
             30                  35                  40 gac gcc aag tcc ggc tgc gag ccg ggc ggt gtc gcc tac tcg tgc gcc        243
Asp Ala Lys Ser Gly Cys Glu Pro Gly Gly Val Ala Tyr Ser Cys Ala
         45                  50                  55 gac cag acc cca tgg gct gtg aac gac gac ttc gcg ctc ggt ttt gct        291
Asp Gln Thr Pro Trp Ala Val Asn Asp Asp Phe Ala Leu Gly Phe Ala
         60                  65                  70 gcc acc tct att gcc ggc agc aat gag gcg ggc tgg tgc tgc gcc tgc        339
Ala Thr Ser Ile Ala Gly Ser Asn Glu Ala Gly Trp Cys Cys Ala Cys
 75                  80                  85 tac gag ctc acc ttc aca tcc ggt cct gtt gct ggc aag aag atg gtc        387
Tyr Glu Leu Thr Phe Thr Ser Gly Pro Val Ala Gly Lys Lys Met Val
 90                  95                 100                 105 gtc cag tcc acc agc act ggc ggt gat ctt ggc agc aac cac ttc gat        435
Val Gln Ser Thr Ser Thr Gly Gly Asp Leu Gly Ser Asn His Phe Asp
             110                 115                 120 ctc aac atc ccc ggc ggc ggc gtc ggc atc ttc gac gga tgc act ccc        483
Leu Asn Ile Pro Gly Gly Gly Val Gly Ile Phe Asp Gly Cys Thr Pro
             125                 130                 135 cag ttc ggc ggt ctg ccc ggc cag cgc tac ggc ggc atc tcg tcc cgc        531
Gln Phe Gly Gly Leu Pro Gly Gln Arg Tyr Gly Gly Ile Ser Ser Arg
         140                 145                 150 aac gag tgc gat cgg ttc ccc gac gcc ctc aag ccc ggc tgc tac tgg        579
Asn Glu Cys Asp Arg Phe Pro Asp Ala Leu Lys Pro Gly Cys Tyr Trp
         155                 160                 165 cgc ttc gac tgg ttc aag aac gcc gac aat ccg agc ttc agc ttc cgt        627
Arg Phe Asp Trp Phe Lys Asn Ala Asp Asn Pro Ser Phe Ser Phe Arg
170                 175                 180                 185 cag gtc cag tgc cca gcc gag ctc gtc gct cgc acc gga tgc cgc cgc        675
Gln Val Gln Cys Pro Ala Glu Leu Val Ala Arg Thr Gly Cys Arg Arg
             190                 195                 200 aac gac gac ggc aac ttc cct gcc gtc cag atc ccc tcc agc agc acc        723
Asn Asp Asp Gly Asn Phe Pro Ala Val Gln Ile Pro Ser Ser Ser Thr
```

```
                   205                 210                 215
agc tct ccg gtc aac cag cct acc agc acc agc acc acg tcc acc tcc      771
Ser Ser Pro Val Asn Gln Pro Thr Ser Thr Ser Thr Thr Ser Thr Ser
        220                 225                 230 acc acc tcg agc ccg cca gtc cag cct acg act ccc agc ggc tgc act      819
Thr Thr Ser Ser Pro Pro Val Gln Pro Thr Thr Pro Ser Gly Cys Thr
        235                 240                 245 gct gag agg tgg gct cag tgc ggc ggc aat ggc tgg agc ggc tgc acc      867
Ala Glu Arg Trp Ala Gln Cys Gly Gly Asn Gly Trp Ser Gly Cys Thr
250                 255                 260                 265 acc tgc gtc gct ggc agc act tgc acg aag att aat gac tgg tac cat      915
Thr Cys Val Ala Gly Ser Thr Cys Thr Lys Ile Asn Asp Trp Tyr His
                270                 275                 280 cag tgc ctg tagacgcagg gcagcttgag ggccttactg gtggccgcaa              964
Gln Cys Leu cgaaatgaca ctcccaatca ctgtattagt tcttgtacat aatttcgtca tccctccagg   1024
gattgtcaca taaatgcaat gaggaacaat gagtac                             1060

<210> SEQ ID NO 2
<211> LENGTH: 305
<212> TYPE: PRT
<213> ORGANISM: Humicola insolens

<400> SEQUENCE: 2

Met Arg Ser Ser Pro Leu Leu Pro Ser Ala Val Val Ala Ala Leu Pro
    -20                 -15                 -10

Val Leu Ala Leu Ala Ala Asp Gly Arg Ser Thr Arg Tyr Trp Asp Cys
 -5              -1   1               5                  10

Cys Lys Pro Ser Cys Gly Trp Ala Lys Lys Ala Pro Val Asn Gln Pro
            15                  20                  25

Val Phe Ser Cys Asn Ala Asn Phe Gln Arg Ile Thr Asp Phe Asp Ala
            30                  35                  40

Lys Ser Gly Cys Glu Pro Gly Gly Val Ala Tyr Ser Cys Ala Asp Gln
        45                  50                  55

Thr Pro Trp Ala Val Asn Asp Asp Phe Ala Leu Gly Phe Ala Ala Thr
60                  65                  70                  75

Ser Ile Ala Gly Ser Asn Glu Ala Gly Trp Cys Cys Ala Cys Tyr Glu
                80                  85                  90

Leu Thr Phe Thr Ser Gly Pro Val Ala Gly Lys Lys Met Val Val Gln
                95                 100                 105

Ser Thr Ser Thr Gly Gly Asp Leu Gly Ser Asn His Phe Asp Leu Asn
            110                 115                 120

Ile Pro Gly Gly Gly Val Gly Ile Phe Asp Gly Cys Thr Pro Gln Phe
        125                 130                 135

Gly Gly Leu Pro Gly Gln Arg Tyr Gly Gly Ile Ser Ser Arg Asn Glu
140                 145                 150                 155

Cys Asp Arg Phe Pro Asp Ala Leu Lys Pro Gly Cys Tyr Trp Arg Phe
                160                 165                 170

Asp Trp Phe Lys Asn Ala Asp Asn Pro Ser Phe Ser Phe Arg Gln Val
            175                 180                 185

Gln Cys Pro Ala Glu Leu Val Ala Arg Thr Gly Cys Arg Arg Asn Asp
        190                 195                 200

Asp Gly Asn Phe Pro Ala Val Gln Ile Pro Ser Ser Ser Thr Ser Ser
    205                 210                 215

Pro Val Asn Gln Pro Thr Ser Thr Ser Thr Thr Ser Thr Ser Thr Thr
```

-continued

```
         220                 225                 230                 235
Ser Ser Pro Pro Val Gln Pro Thr Thr Pro Ser Gly Cys Thr Ala Glu
                240                 245                 250
Arg Trp Ala Gln Cys Gly Gly Asn Gly Trp Ser Gly Cys Thr Thr Cys
            255                 260                 265
Val Ala Gly Ser Thr Cys Thr Lys Ile Asn Asp Trp Tyr His Gln Cys
        270                 275                 280
Leu

<210> SEQ ID NO 3
<211> LENGTH: 1473
<212> TYPE: DNA
<213> ORGANISM: Fusarium oxysporum
<220> FEATURE:
<221> NAME/KEY: CDS
<222> LOCATION: (97)..(1224)

<400> SEQUENCE: 3
gaattcgcgg ccgctcattc acttcattca ttctttagaa ttacatacac tctctttcaa      60
aacagtcact ctttaaacaa acaactttt gcaaca atg cga tct tac act ctt       114
                                        Met Arg Ser Tyr Thr Leu
                                          1               5 ctc gcc ctg gcc ggc cct ctc gcc gtg agt gct gct tct gga agc ggt     162
Leu Ala Leu Ala Gly Pro Leu Ala Val Ser Ala Ala Ser Gly Ser Gly
             10                  15                  20 cac tct act cga tac tgg gat tgc tgc aag cct tct tgc tct tgg agc     210
His Ser Thr Arg Tyr Trp Asp Cys Cys Lys Pro Ser Cys Ser Trp Ser
         25                  30                  35 gga aag gct gct gtc aac gcc cct gct tta act tgt gat aag aac gac     258
Gly Lys Ala Ala Val Asn Ala Pro Ala Leu Thr Cys Asp Lys Asn Asp
     40                  45                  50 aac ccc att tcc aac acc aat gct gtc aac ggt tgt gag ggt ggt ggt     306
Asn Pro Ile Ser Asn Thr Asn Ala Val Asn Gly Cys Glu Gly Gly Gly
 55                  60                  65                  70 tct gct tat gct tgc acc aac tac tct ccc tgg gct gtc aac gat gag     354
Ser Ala Tyr Ala Cys Thr Asn Tyr Ser Pro Trp Ala Val Asn Asp Glu
                 75                  80                  85 ctt gcc tac ggt ttc gct gct acc aag atc tcc ggt ggc tcc gag gcc     402
Leu Ala Tyr Gly Phe Ala Ala Thr Lys Ile Ser Gly Gly Ser Glu Ala
             90                  95                 100 agc tgg tgc tgt gct tgc tat gct ttg acc ttc acc act ggc ccc gtc     450
Ser Trp Cys Cys Ala Cys Tyr Ala Leu Thr Phe Thr Thr Gly Pro Val
         105                 110                 115 aag ggc aag aag atg atc gtc cag tcc acc aac act gga ggt gat ctc     498
Lys Gly Lys Lys Met Ile Val Gln Ser Thr Asn Thr Gly Gly Asp Leu
     120                 125                 130 ggc gac aac cac ttc gat ctc atg atg ccc ggc ggt gtc ggt atc         546
Gly Asp Asn His Phe Asp Leu Met Met Pro Gly Gly Gly Val Gly Ile
135                 140                 145                 150 ttc gac ggc tgc acc tct gag ttc ggc aag gct ctc ggc ggt gcc cag     594
Phe Asp Gly Cys Thr Ser Glu Phe Gly Lys Ala Leu Gly Gly Ala Gln
                155                 160                 165 tac ggc ggt atc tcc tcc cga agc gaa tgt gat agc tac ccc gag ctt     642
Tyr Gly Gly Ile Ser Ser Arg Ser Glu Cys Asp Ser Tyr Pro Glu Leu
            170                 175                 180 ctc aag gac ggt tgc cac tgg cga ttc gac tgg ttc gag aac gcc gac     690
Leu Lys Asp Gly Cys His Trp Arg Phe Asp Trp Phe Glu Asn Ala Asp
        185                 190                 195 aac cct gac ttc acc ttt gag cag gtt cag tgc ccc aag gct ctc ctc     738
```

-continued

```
Asn Pro Asp Phe Thr Phe Glu Gln Val Gln Cys Pro Lys Ala Leu Leu
    200                 205                 210 gac atc agt gga tgc aag cgt gat gac gac tcc agc ttc cct gcc ttc      786
Asp Ile Ser Gly Cys Lys Arg Asp Asp Asp Ser Ser Phe Pro Ala Phe
215                 220                 225                 230 aag gtt gat acc tcg gcc agc aag ccc cag ccc tcc agc tcc gct aag      834
Lys Val Asp Thr Ser Ala Ser Lys Pro Gln Pro Ser Ser Ser Ala Lys
                235                 240                 245 aag acc acc tcc gct gct gct gcc gct cag ccc cag aag acc aag gat      882
Lys Thr Thr Ser Ala Ala Ala Ala Ala Gln Pro Gln Lys Thr Lys Asp
            250                 255                 260 tcc gct cct gtt gtc cag aag tcc tcc acc aag cct gcc gct cag ccc      930
Ser Ala Pro Val Val Gln Lys Ser Ser Thr Lys Pro Ala Ala Gln Pro
        265                 270                 275 gag cct act aag ccc gcc gac aag ccc cag acc gac aag cct gtc gcc      978
Glu Pro Thr Lys Pro Ala Asp Lys Pro Gln Thr Asp Lys Pro Val Ala
    280                 285                 290 acc aag cct gct gct acc aag ccc gtc caa cct gtc aac aag ccc aag     1026
Thr Lys Pro Ala Ala Thr Lys Pro Val Gln Pro Val Asn Lys Pro Lys
295                 300                 305                 310 aca acc cag aac gtc cgt gga acc aaa acc cga gga agc tgc ccg gcc     1074
Thr Thr Gln Asn Val Arg Gly Thr Lys Thr Arg Gly Ser Cys Pro Ala
                315                 320                 325 aag act gac gct acc gcc aag gcc tcc gtt gtc cct gct tat tac cag     1122
Lys Thr Asp Ala Thr Ala Lys Ala Ser Val Val Pro Ala Tyr Tyr Gln
            330                 335                 340 tgt ggt ggt tcc aag tcc gct tat ccc aac ggc aac ctc gct tgc gct     1170
Cys Gly Gly Ser Lys Ser Ala Tyr Pro Asn Gly Asn Leu Ala Cys Ala
        345                 350                 355 act gga agc aag tgt gtc aag cag aac gag tac tac tcc cag tgt gtc     1218
Thr Gly Ser Lys Cys Val Lys Gln Asn Glu Tyr Tyr Ser Gln Cys Val
    360                 365                 370 ccc aac taaatggtag atccatcggt tgtggaagag actatgcgtc tcagaaggga      1274
Pro Asn
375 tcctctcatg agcaggcttg tcattgtata gcatggcatc ctggaccaag tgttcgaccc   1334 ttgttgtaca tagtatatct tcattgtata tatttagaca catagatagc ctcttgtcag   1394 cgacaactgg ctacaaaaga cttggcaggc ttgttcaata ttgacacagt ttcctccata   1454 aaaaaaaaaa aaaaaaaaa                                                1473

<210> SEQ ID NO 4
<211> LENGTH: 376
<212> TYPE: PRT
<213> ORGANISM: Fusarium oxysporum

<400> SEQUENCE: 4

Met Arg Ser Tyr Thr Leu Leu Ala Leu Ala Gly Pro Leu Ala Val Ser
  1               5                  10                  15

Ala Ala Ser Gly Ser Gly His Ser Thr Arg Tyr Trp Asp Cys Cys Lys
            20                  25                  30

Pro Ser Cys Ser Trp Ser Gly Lys Ala Ala Val Asn Ala Pro Ala Leu
        35                  40                  45

Thr Cys Asp Lys Asn Asp Asn Pro Ile Ser Asn Thr Asn Ala Val Asn
    50                  55                  60

Gly Cys Glu Gly Gly Gly Ser Ala Tyr Ala Cys Thr Asn Tyr Ser Pro
 65                  70                  75                  80

Trp Ala Val Asn Asp Glu Leu Ala Tyr Gly Phe Ala Ala Thr Lys Ile
```

85                    90                    95
Ser Gly Gly Ser Glu Ala Ser Trp Cys Cys Ala Cys Tyr Ala Leu Thr
                100                   105                   110

Phe Thr Thr Gly Pro Val Lys Gly Lys Lys Met Ile Val Gln Ser Thr
        115                   120                   125

Asn Thr Gly Gly Asp Leu Gly Asp Asn His Phe Asp Leu Met Met Pro
    130                   135                   140

Gly Gly Gly Val Gly Ile Phe Asp Gly Cys Thr Ser Glu Phe Gly Lys
145                   150                   155                   160

Ala Leu Gly Gly Ala Gln Tyr Gly Gly Ile Ser Ser Arg Ser Glu Cys
                165                   170                   175

Asp Ser Tyr Pro Glu Leu Leu Lys Asp Gly Cys His Trp Arg Phe Asp
            180                   185                   190

Trp Phe Glu Asn Ala Asp Asn Pro Asp Phe Thr Phe Glu Gln Val Gln
        195                   200                   205

Cys Pro Lys Ala Leu Leu Asp Ile Ser Gly Cys Lys Arg Asp Asp Asp
    210                   215                   220

Ser Ser Phe Pro Ala Phe Lys Val Asp Thr Ser Ala Ser Lys Pro Gln
225                   230                   235                   240

Pro Ser Ser Ser Ala Lys Lys Thr Thr Ser Ala Ala Ala Ala Gln
                245                   250                   255

Pro Gln Lys Thr Lys Asp Ser Ala Pro Val Val Gln Lys Ser Ser Thr
            260                   265                   270

Lys Pro Ala Ala Gln Pro Glu Pro Thr Lys Pro Ala Asp Lys Pro Gln
        275                   280                   285

Thr Asp Lys Pro Val Ala Thr Lys Pro Ala Ala Thr Lys Pro Val Gln
290                   295                   300

Pro Val Asn Lys Pro Lys Thr Thr Gln Asn Val Arg Gly Thr Lys Thr
305                   310                   315                   320

Arg Gly Ser Cys Pro Ala Lys Thr Asp Ala Thr Ala Lys Ala Ser Val
                325                   330                   335

Val Pro Ala Tyr Tyr Gln Cys Gly Gly Ser Lys Ser Ala Tyr Pro Asn
            340                   345                   350

Gly Asn Leu Ala Cys Ala Thr Gly Ser Lys Cys Val Lys Gln Asn Glu
        355                   360                   365

Tyr Tyr Ser Gln Cys Val Pro Asn
370                   375

<210> SEQ ID NO 5
<211> LENGTH: 807
<212> TYPE: DNA
<213> ORGANISM: Unknown Organism
<220> FEATURE:
<223> OTHER INFORMATION: Description of Unknown Organism:Organism
      encoding an endoglucanase enzyme
<220> FEATURE:
<221> NAME/KEY: CDS
<222> LOCATION: (10)..(711)
<220> FEATURE:
<221> NAME/KEY: mat_peptide
<222> LOCATION: (73)..(711)
<220> FEATURE:
<221> NAME/KEY: sig_peptide
<222> LOCATION: (10)..(72)

<400> SEQUENCE: 5 ggatccaag atg cgt tcc tcc ccc ctc ctc ccg tcc gcc gtt gtg gcc gcc     51
          Met Arg Ser Ser Pro Leu Leu Pro Ser Ala Val Val Ala Ala
              -20                 -15                 -10

```
ctg ccg gtg ttg gcc ctt gcc gct gat ggc agg tcc acc cgc tac tgg    99
Leu Pro Val Leu Ala Leu Ala Ala Asp Gly Arg Ser Thr Arg Tyr Trp
        -5              -1  1               5 gac tgc tgc aag cct tcg tgc ggc tgg gcc aag aag gct ccc gtg aac   147
Asp Cys Cys Lys Pro Ser Cys Gly Trp Ala Lys Lys Ala Pro Val Asn
10                  15                  20                  25 cag cct gtc ttt tcc tgc aac gcc aac ttc cag cgt atc acg gac ttc   195
Gln Pro Val Phe Ser Cys Asn Ala Asn Phe Gln Arg Ile Thr Asp Phe
                30                  35                  40 gac gcc aag tcc ggc tgc gag ccg ggc ggt gtc gcc tac tcg tgc gcc   243
Asp Ala Lys Ser Gly Cys Glu Pro Gly Gly Val Ala Tyr Ser Cys Ala
            45                  50                  55 gac cag acc cca tgg gct gtg aac gac gac ttc gcg ctc ggt ttt gct   291
Asp Gln Thr Pro Trp Ala Val Asn Asp Asp Phe Ala Leu Gly Phe Ala
        60                  65                  70 gcc acc tct att gcc ggc agc aat gag gcg ggc tgg tgc tgc gcc tgc   339
Ala Thr Ser Ile Ala Gly Ser Asn Glu Ala Gly Trp Cys Cys Ala Cys
    75                  80                  85 tac gag ctc acc ttc aca tcc ggt cct gtt gct ggc aag aag atg gtc   387
Tyr Glu Leu Thr Phe Thr Ser Gly Pro Val Ala Gly Lys Lys Met Val
90                  95                  100                 105 gtc cag tcc acc agc act ggc ggt gat ctt ggc agc aac cac ttc gat   435
Val Gln Ser Thr Ser Thr Gly Gly Asp Leu Gly Ser Asn His Phe Asp
                110                 115                 120 ctc aac atc ccc ggc ggc ggc gtc ggc atc ttc gac gga tgc act ccc   483
Leu Asn Ile Pro Gly Gly Gly Val Gly Ile Phe Asp Gly Cys Thr Pro
            125                 130                 135 cag ttc ggc ggt ctg ccc ggc cag cgc tac ggc ggc atc tcg tcc cgc   531
Gln Phe Gly Gly Leu Pro Gly Gln Arg Tyr Gly Gly Ile Ser Ser Arg
        140                 145                 150 aac gag tgc gat cgg ttc ccc gac gcc ctc aag ccc ggc tgc tac tgg   579
Asn Glu Cys Asp Arg Phe Pro Asp Ala Leu Lys Pro Gly Cys Tyr Trp
    155                 160                 165 cgc ttc gac tgg ttc aag aac gcc gac aat ccg agc ttc agc ttc cgt   627
Arg Phe Asp Trp Phe Lys Asn Ala Asp Asn Pro Ser Phe Ser Phe Arg
170                 175                 180                 185 cag gtc cag tgc cca gcc gag ctc gtc gct cgc acc gga tgc cgc cgc   675
Gln Val Gln Cys Pro Ala Glu Leu Val Ala Arg Thr Gly Cys Arg Arg
                190                 195                 200 aac gac gac ggc aac ttc cct gcc gtc cag atc ccc cgaaatgaca        721
Asn Asp Asp Gly Asn Phe Pro Ala Val Gln Ile Pro
            205                 210 ctcccaatca ctgtattagt tcttgtacat aatttcgtca tccctccagg gattgtcaca    781
taaatgcaat gaggaacaat gagtac                                        807

<210> SEQ ID NO 6
<211> LENGTH: 234
<212> TYPE: PRT
<213> ORGANISM: Unknown Organism
<220> FEATURE:
<223> OTHER INFORMATION: Description of Unknown Organism:Organism
      encoding an endoglucanase enzyme

<400> SEQUENCE: 6

Met Arg Ser Ser Pro Leu Leu Pro Ser Ala Val Val Ala Ala Leu Pro
    -20                 -15                 -10

Val Leu Ala Leu Ala Ala Asp Gly Arg Ser Thr Arg Tyr Trp Asp Cys
-5              -1  1               5                   10

Cys Lys Pro Ser Cys Gly Trp Ala Lys Lys Ala Pro Val Asn Gln Pro
```

```
                    15                  20                  25
Val Phe Ser Cys Asn Ala Asn Phe Gln Arg Ile Thr Asp Phe Asp Ala
            30                  35                  40

Lys Ser Gly Cys Glu Pro Gly Val Ala Tyr Ser Cys Ala Asp Gln
 45                  50                  55

Thr Pro Trp Ala Val Asn Asp Asp Phe Ala Leu Gly Phe Ala Ala Thr
 60                  65                  70                  75

Ser Ile Ala Gly Ser Asn Glu Ala Gly Trp Cys Cys Ala Cys Tyr Glu
                80                  85                  90

Leu Thr Phe Thr Ser Gly Pro Val Ala Gly Lys Lys Met Val Val Gln
                95                 100                 105

Ser Thr Ser Thr Gly Gly Asp Leu Gly Ser Asn His Phe Asp Leu Asn
            110                 115                 120

Ile Pro Gly Gly Val Gly Ile Phe Asp Gly Cys Thr Pro Gln Phe
125                 130                 135

Gly Gly Leu Pro Gly Gln Arg Tyr Gly Gly Ile Ser Ser Arg Asn Glu
140                 145                 150                 155

Cys Asp Arg Phe Pro Asp Ala Leu Lys Pro Gly Cys Tyr Trp Arg Phe
                160                 165                 170

Asp Trp Phe Lys Asn Ala Asp Asn Pro Ser Phe Ser Phe Arg Gln Val
            175                 180                 185

Gln Cys Pro Ala Glu Leu Val Ala Arg Thr Gly Cys Arg Arg Asn Asp
        190                 195                 200

Asp Gly Asn Phe Pro Ala Val Gln Ile Pro
    205                 210

<210> SEQ ID NO 7
<211> LENGTH: 984
<212> TYPE: DNA
<213> ORGANISM: Unknown Organism
<220> FEATURE:
<223> OTHER INFORMATION: Description of Unknown Organism:Organism
      encoding an endoglucanase enzyme
<220> FEATURE:
<221> NAME/KEY: CDS
<222> LOCATION: (97)..(735)

<400> SEQUENCE: 7
gaattcgcgg ccgctcattc acttcattca ttctttagaa ttacatacac tctctttcaa        60
aacagtcact ctttaaacaa aacaactttt gcaaca atg cga tct tac act ctt        114
                                         Met Arg Ser Tyr Thr Leu
                                           1               5 ctc gcc ctg gcc ggc cct ctc gcc gtg agt gct gct tct gga agc ggt        162
Leu Ala Leu Ala Gly Pro Leu Ala Val Ser Ala Ala Ser Gly Ser Gly
         10                  15                  20 cac tct act cga tac tgg gat tgc tgc aag cct tct tgc tct tgg agc        210
His Ser Thr Arg Tyr Trp Asp Cys Cys Lys Pro Ser Cys Ser Trp Ser
         25                  30                  35 gga aag gct gct gtc aac gcc cct gct tta act tgt gat aag aac gac        258
Gly Lys Ala Ala Val Asn Ala Pro Ala Leu Thr Cys Asp Lys Asn Asp
 40                  45                  50 aac ccc att tcc aac acc aat gct gtc aac ggt tgt gag ggt ggt ggt        306
Asn Pro Ile Ser Asn Thr Asn Ala Val Asn Gly Cys Glu Gly Gly Gly
 55                  60                  65                  70 tct gct tat gct tgc acc aac tac tct ccc tgg gct gtc aac gat gag        354
Ser Ala Tyr Ala Cys Thr Asn Tyr Ser Pro Trp Ala Val Asn Asp Glu
             75                  80                  85 ctt gcc tac ggt ttc gct gct acc aag atc tcc ggt ggc tcc gag gcc        402
```

```
Leu Ala Tyr Gly Phe Ala Ala Thr Lys Ile Ser Gly Gly Ser Glu Ala
            90                  95                  100 agc tgg tgc tgt gct tgc tat gct ttg acc ttc acc act ggc ccc gtc   450
Ser Trp Cys Cys Ala Cys Tyr Ala Leu Thr Phe Thr Thr Gly Pro Val
        105                 110                 115 aag ggc aag aag atg atc gtc cag tcc acc aac act gga ggt gat ctc   498
Lys Gly Lys Lys Met Ile Val Gln Ser Thr Asn Thr Gly Gly Asp Leu
    120                 125                 130 ggc gac aac cac ttc gat ctc atg atg ccc ggc ggt gtc ggt atc       546
Gly Asp Asn His Phe Asp Leu Met Met Pro Gly Gly Val Gly Ile
135                 140                 145                 150 ttc gac ggc tgc acc tct gag ttc ggc aag gct ctc ggc ggt gcc cag   594
Phe Asp Gly Cys Thr Ser Glu Phe Gly Lys Ala Leu Gly Gly Ala Gln
                155                 160                 165 tac ggc ggt atc tcc tcc cga agc gaa tgt gat agc tac ccc gag ctt   642
Tyr Gly Gly Ile Ser Ser Arg Ser Glu Cys Asp Ser Tyr Pro Glu Leu
            170                 175                 180 ctc aag gac ggt tgc cac tgg cga ttc gac tgg ttc gag aac gcc gac   690
Leu Lys Asp Gly Cys His Trp Arg Phe Asp Trp Phe Glu Asn Ala Asp
        185                 190                 195 aac cct gac ttc acc ttt gag cag gtt cag tgc ccc aag gct ctc       735
Asn Pro Asp Phe Thr Phe Glu Gln Val Gln Cys Pro Lys Ala Leu
    200                 205                 210 taaatggtag atccatcggt tgtggaagag actatgcgtc tcagaaggga tcctctcatg   795
agcaggcttg tcattgtata gcatggcatc ctggaccaag tgttcgaccc ttgttgtaca   855
tagtatatct tcattgtata tatttagaca catagatagc ctcttgtcag cgacaactgg   915
ctacaaaaga cttggcaggc ttgttcaata ttgacacagt ttcctccata aaaaaaaaaa   975
aaaaaaaaa                                                          984

<210> SEQ ID NO 8
<211> LENGTH: 213
<212> TYPE: PRT
<213> ORGANISM: Unknown Organism
<220> FEATURE:
<223> OTHER INFORMATION: Description of Unknown Organism:Organism
      encoding an endoglucanase enzyme

<400> SEQUENCE: 8

Met Arg Ser Tyr Thr Leu Leu Ala Leu Ala Gly Pro Leu Ala Val Ser
1               5                   10                  15

Ala Ala Ser Gly Ser Gly His Ser Thr Arg Tyr Trp Asp Cys Cys Lys
            20                  25                  30

Pro Ser Cys Ser Trp Ser Gly Lys Ala Ala Val Asn Ala Pro Ala Leu
        35                  40                  45

Thr Cys Asp Lys Asn Asp Asn Pro Ile Ser Asn Thr Asn Ala Val Asn
    50                  55                  60

Gly Cys Glu Gly Gly Gly Ser Ala Tyr Ala Cys Thr Asn Tyr Ser Pro
65                  70                  75                  80

Trp Ala Val Asn Asp Glu Leu Ala Tyr Gly Phe Ala Ala Thr Lys Ile
                85                  90                  95

Ser Gly Gly Ser Glu Ala Ser Trp Cys Cys Ala Cys Tyr Ala Leu Thr
            100                 105                 110

Phe Thr Thr Gly Pro Val Lys Gly Lys Lys Met Ile Val Gln Ser Thr
        115                 120                 125

Asn Thr Gly Gly Asp Leu Gly Asp Asn His Phe Asp Leu Met Met Pro
    130                 135                 140
```

```
                                     -continued

Gly Gly Gly Val Gly Ile Phe Asp Gly Cys Thr Ser Glu Phe Gly Lys
145             150                 155                 160

Ala Leu Gly Gly Ala Gln Tyr Gly Gly Ile Ser Ser Arg Ser Glu Cys
                165                 170             175

Asp Ser Tyr Pro Glu Leu Leu Lys Asp Gly Cys His Trp Arg Phe Asp
            180                 185                 190

Trp Phe Glu Asn Ala Asp Asn Pro Asp Phe Thr Phe Glu Gln Val Gln
        195                 200             205

Cys Pro Lys Ala Leu
        210
```

Having thus described the invention in detail, it will be clear to those skilled in the art that various changes may be made without departing from the scope of the invention and the invention is not to be considered limited to what is described in the specification.

What is claimed is:

1. A detergent composition comprising:
   (a) at least 1% by weight of a surfactant;
   (b) at least 1% by weight of a builder;
   (c) an effective amount of an enzymatic mixture capable of degrading cellulose characterized by a combination of at least two cellulases, of which one is a surface-active cellulase and one is a nonsurface-active cellulase;

whereby said nonsurface-active cellulase and said surface-active cellulase are in a weight ratio of from 1:2 to 20:1 in said detergent composition;

and wherein both said surface-active cellulase and said nonsurface-active cellulase comprise an endoglucanase enzyme having an isoelectric point of 5.1 which is free of cellobiohydrolase activity.

2. A detergent composition according to claim 1 wherein said surface-active cellulase is an endoglucanase enzyme having the amino acid sequence shown in the appended listing SEQ ID NO:2.

3. A detergent composition according to claim 2 wherein said endoglucanase enzyme is produced by a species of Humicola.

4. A detergent composition according to claim 2 wherein said endoglucanase enzyme is produced by a method comprising cultivating a host cell transformed with a recombinant DNA vector carrying a DNA sequence encoding said endoglucanase enzyme, or a precursor of said endoglucanase enzyme, of said surface-active cellulase, and DNA sequences encoding functions permitting the expression of said DNA sequence, or a precursor thereof, in a culture medium under conditions permitting the expression of said endoglucanase enzyme, or a precursor thereof, of said surface-active cellulase and recovering said endoglucanse enzyme from said culture medium.

5. A detergent composition according to claim 4 wherein said host cell is a microorganism selected from the group consisting of the genera Aspergillus, Trichoderma, Hansenula, Saccharomyces, Streptomyces, Bacillus and Eschericia.

6. A detergent composition according to claim 4 wherein said DNA sequence encoding said endoglucanase enzyme of said surface-active cellulase is as shown in the appended listing SEQ ID NO:1.

7. A detergent composition according to claim 1 wherein said surface-active cellulase is an endoglucanase enzyme having the amino acid sequence shown in the appended listing SEQ ID NO:4.

8. A detergent composition according to claim 7 wherein said endoglucanase enzyme is produced by a species of Fusarium.

9. A detergent composition according to claim 7 wherein said endoglucanase enzyme is produced by a method comprising cultivating a host cell transformed with a recombinant DNA vector carrying a DNA sequence encoding said endoglucanase enzyme, or a precursor of said endoglucanase enzyme, of said surface-active cellulase, and DNA sequences encoding functions permitting the expression of said DNA sequence, or a precursor thereof, in a culture medium under conditions permitting the expression of said endoglucanase enzyme, or a precursor thereof, of said surface-active cellulase and recovering said endoglucanse enzyme from said culture medium.

10. A detergent composition according to claim 9 wherein said host cell is a microorganism selected from the group consisting of the genera Aspergillus, Trichoderma, Hansenula, Saccharomyces, Streptomyces, Bacillus and Eschericia.

11. A detergent composition according to claim 7 wherein said DNA sequence encoding said endoglucanase enzyme of said surface-active cellulase is as shown in the appended listing SEQ ID NO:3.

12. A detergent composition according to claim 1 wherein said nonsurface-active cellulase is an endoglucanase enzyme having the amino acid sequence shown in the appended listing SEQ ID NO:6.

13. A detergent composition according to claim 12 wherein said endoglucanase enzyme is produced by a method comprising cultivating a host cell transformed with a recombinant DNA vector carrying a DNA sequence encoding said endoglucanase enzyme, or a precursor of said endoglucanase enzyme, of said nonsurface-active cellulase, and DNA sequences encoding functions permitting the expression of said DNA sequence, or a precursor thereof, in a culture medium under conditions permitting the expression of said endoglucanase enzyme, or a precursor thereof, of said nonsurface-active cellulase and recovering said endoglucanse enzyme from said culture medium.

14. A detergent composition according to claim 13 wherein said host cell is a microorganism selected from the group consisting of the genera Aspergillus, Trichoderma, Hansenula, Saccharomyces, Streptomyces, Bacillus and Eschericia.

15. A detergent composition according to claim 13 wherein said DNA sequence encoding said endoglucanase of said nonsurface-active cellulase is as shown in the appended listing SEQ ID NO:5.

16. A detergent composition according to claim 1 wherein said nonsurface-active cellulase is an endoglucanase enzyme having the amino acid sequence shown in the appended listing SEQ ID NO:8.

17. A detergent composition according to claim 16 wherein said endoglucanase enzyme is produced by a method comprising cultivating a host cell transformed with a recombinant DNA vector carrying a DNA sequence encoding said endoglucanase enzyme, or a precursor of said endoglucanase enzyme, of said nonsurface-active cellulase, and DNA sequences encoding functions permitting the expression of said DNA sequence, or a precursor thereof, in a culture medium under conditions permitting the expression of said endoglucanase enzyme, or a precursor thereof, of said nonsurface-active cellulase and recovering said endoglucanse enzyme from said culture medium.

18. A detergent composition according to claim 17 wherein said host cell is a microorganism selected from the group consisting of the genera Aspergillus, Trichoderma, Hansenula, Saccharomyces, Streptomyces, Bacillus and Eschericia.

19. A detergent composition according to claim 17 wherein said DNA sequence encoding said endoglucanase enzyme of said nonsurface-active cellulase is as shown in the appended listing SEQ ID NO:7.

20. A detergent composition according to claim 1 wherein the surface-active cellulase provides from about 5% to about 67% and the nonsurface-active cellulase provides from about 33% to about 95% of the total cellulase activity in the enzymatic mixture.

21. A detergent composition according to claim 1 which is in the form of granules, agglomerates or mixtures thereof.

22. A detergent composition according to claim 1 wherein said surface-active cellulase and said nonsurface-active cellulase are present in an amount such that the amount of total cellulase enzyme delivered to the wash solution is from about 0.005 to about 1 mg/liter of wash solution.

23. A detergent composition according to claim 1 wherein said surface-active cellulase comprises a homogeneous endoglucanase enzyme having an endoglucanase activity of at least 50 CMC-endoase units per milligram of total protein.

24. A detergent composition according to claim 1 wherein said nonsurface-active cellulase comprises a homogeneous endoglucanase enzyme having an endoglucanase activity of at least 50 CMC-endoase units per milligram of total protein.

25. A method of laundering soiled fabrics comprising the step of contacting said fabrics with a detergent composition according to claim 1 in an aqueous laundering solution wherein from about 2,000 parts per million to about 10,000 parts per million of said detergent composition is present in said aqueous laundering solution.

26. An enzymatic mixture comprising:
(a) from about 0.01 % to about 2% by weight of a surface-active cellulase;
(b) from about 0.02% to about 3% by weight of a nonsurface-active cellulase;
(c) the balance water;
whereby the nonsurface-active cellulase and the surface-active cellulase are in a weight ratio of from about 1:2 to about 20:1 in said enzymatic mixture; and wherein both said surface-active cellulase and said nonsurface-active cellulase comprise an endoglucanase enzyme having an isoelectric point of 5.1 which is free of cellobiohydrolase activity.

* * * * *